(12) United States Patent
Balbierz et al.

(10) Patent No.: US 10,368,862 B2
(45) Date of Patent: *Aug. 6, 2019

(54) MULTI-FIRE STAPLING METHODS

(71) Applicant: Boston Scientific Scimed, Inc., Maple Grove, MN (US)

(72) Inventors: Daniel J. Balbierz, Redwood City, CA (US); Pablo R. Hambly, San Mateo, CA (US); Jason S. Stewart, Redwood City, CA (US); David Cole, Weybridge, VT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 275 days.

This patent is subject to a terminal disclaimer.

(21) Appl. No.: 15/246,384

(22) Filed: Aug. 24, 2016

(65) Prior Publication Data

US 2016/0361059 A1 Dec. 15, 2016

Related U.S. Application Data

(60) Continuation of application No. 14/259,781, filed on Apr. 23, 2014, now Pat. No. 9,451,956, which is a
(Continued)

(51) Int. Cl.
*A61B 17/068* (2006.01)
*A61B 17/072* (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC . A61B 17/068; A61B 17/0686; A61B 17/072; A61B 17/07207; A61B 17/115;
(Continued)

(56) References Cited

U.S. PATENT DOCUMENTS

| | | | |
|---|---|---|---|
| 1,408,865 | A | 3/1922 | Cowell |
| 3,663,965 | A | 5/1972 | Culp et al. |

(Continued)

FOREIGN PATENT DOCUMENTS

| | | |
|---|---|---|
| AU | 6296642 | 10/1992 |
| CH | 680263 A5 | 7/1992 |

(Continued)

OTHER PUBLICATIONS

Felsher J., et al., "Mucosal Apposition in Endoscopic Suturing," Gastrointestinal Endoscopy, 2003, vol. 58 (6), pp. 867-870.
(Continued)

*Primary Examiner* — Scott A Smith
(74) *Attorney, Agent, or Firm* — Bookoff McAndrews, PLLC

(57) ABSTRACT

A staple housing includes an array of staples each in a staple delivery position or "ready position" ready to be fired into target tissue. A staple driver is advanceable to drive the ready-position staples from the staple head into the tissue using staple pushers. During use, the staples in the ready positions are simultaneously fired into the target tissue using the staple pushers, forming an array of staples in the target tissue. After the array has been fired, one or more feed mechanisms within the staple housing advance a second group of staples from one or more staple storage locations into the ready positions in preparation for firing of the second group of staples.

20 Claims, 20 Drawing Sheets

Related U.S. Application Data continuation of application No. 13/089,216, filed on Apr. 18, 2011, now Pat. No. 8,747,421, which is a division of application No. 12/268,404, filed on Nov. 10, 2008, now Pat. No. 7,934,631.

(51) Int. Cl.
*A61B 17/115* (2006.01)
*A61F 5/00* (2006.01)
*A61B 17/00* (2006.01)

(52) U.S. Cl.
CPC .......... *A61B 17/115* (2013.01); *A61F 5/0086* (2013.01); *A61B 2017/00398* (2013.01); *A61B 2017/07214* (2013.01); *A61B 2017/07228* (2013.01); *A61B 2017/07271* (2013.01)

(58) Field of Classification Search
CPC ...... A61B 17/1155; A61B 2017/07214; A61B 2017/00398
USPC .............. 227/19, 176.1, 175.2, 178.1, 180.1; 606/139, 153, 219
See application file for complete search history.

(56) References Cited

U.S. PATENT DOCUMENTS

| | | |
|---|---|---|
| 4,134,405 A | 1/1979 | Smit |
| 4,207,890 A | 6/1980 | Mamajek et al. |
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |
| 4,485,805 A | 12/1984 | Foster, Jr. |
| 4,501,264 A | 2/1985 | Rockey |
| 4,607,618 A | 8/1986 | Angelchik |
| 4,612,933 A | 9/1986 | Brinkerhoff et al. |
| 4,617,932 A | 10/1986 | Kornberg |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galtier |
| 4,846,836 A | 7/1989 | Reich |
| 4,848,367 A | 7/1989 | Avant et al. |
| 4,899,747 A | 2/1990 | Garren et al. |
| 4,925,446 A | 5/1990 | Garay et al. |
| 4,941,623 A | 7/1990 | Pruitt |
| 4,946,440 A | 8/1990 | Hall |
| 4,969,896 A | 11/1990 | Shors |
| 4,997,084 A | 3/1991 | Opie et al. |
| 5,006,106 A | 4/1991 | Angelchik |
| 5,037,021 A | 8/1991 | Mills et al. |
| 5,061,275 A | 10/1991 | Wallsten et al. |
| 5,084,061 A | 1/1992 | Gau et al. |
| 5,088,979 A | 2/1992 | Filipi et al. |
| 5,163,952 A | 11/1992 | Froix |
| 5,188,274 A | 2/1993 | Moeinzadeh et al. |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,263,629 A | 11/1993 | Trumbull et al. |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shlain |
| 5,355,897 A | 10/1994 | Pietrafitta et al. |
| 5,401,241 A | 3/1995 | Delany |
| 5,403,326 A | 4/1995 | Harrison et al. |
| 5,405,377 A | 4/1995 | Cragg |
| 5,413,267 A | 5/1995 | Solyntjes et al. |
| 5,431,673 A | 7/1995 | Summers et al. |
| 5,470,006 A | 11/1995 | Rodak |
| 5,486,187 A | 1/1996 | Schenck |
| 5,514,176 A | 5/1996 | Bosley, Jr. |
| 5,535,935 A | 7/1996 | Vidal et al. |
| 5,542,949 A | 8/1996 | Yoon |
| 5,562,239 A | 10/1996 | Boiarski et al. |
| 5,571,116 A | 11/1996 | Bolanos et al. |
| 5,577,654 A | 11/1996 | Bishop |
| 5,593,434 A | 1/1997 | Williams |
| 5,597,107 A | 1/1997 | Knodel et al. |
| 5,609,624 A | 3/1997 | Kalis |
| 5,628,786 A | 5/1997 | Banas et al. |
| 5,630,539 A | 5/1997 | Plyley et al. |
| 5,647,526 A | 7/1997 | Green et al. |
| 5,653,743 A | 8/1997 | Martin |
| 5,662,259 A | 9/1997 | Yoo |
| 5,662,713 A | 9/1997 | Andersen et al. |
| 5,673,841 A | 10/1997 | Schulze et al. |
| 5,674,241 A | 10/1997 | Bley et al. |
| 5,706,998 A | 1/1998 | Plyley et al. |
| 5,709,657 A | 1/1998 | Zimmon |
| 5,720,776 A | 2/1998 | Chuter et al. |
| 5,749,918 A | 5/1998 | Hogendijk et al. |
| 5,752,644 A | 5/1998 | Bolanos et al. |
| 5,762,255 A | 6/1998 | Chrisman et al. |
| 5,771,903 A | 6/1998 | Jakobsson |
| 5,785,684 A | 7/1998 | Zimmon |
| 5,792,119 A | 8/1998 | Marx |
| 5,820,584 A | 10/1998 | Crabb |
| 5,833,695 A | 11/1998 | Yoon |
| 5,839,639 A | 11/1998 | Sauer et al. |
| 5,848,964 A | 12/1998 | Samuels |
| 5,855,311 A | 1/1999 | Hamblin et al. |
| 5,855,601 A | 1/1999 | Bessler et al. |
| 5,856,445 A | 1/1999 | Korsmeyer |
| 5,861,036 A | 1/1999 | Godin |
| 5,868,141 A | 2/1999 | Ellias |
| 5,887,594 A | 3/1999 | Locicero, III |
| 5,897,562 A | 4/1999 | Bolanos et al. |
| 5,910,144 A | 6/1999 | Hayashi |
| 5,922,019 A | 7/1999 | Hankh et al. |
| 5,947,983 A | 9/1999 | Solar et al. |
| 5,993,473 A | 11/1999 | Chan et al. |
| 5,993,483 A | 11/1999 | Gianotti |
| 6,016,848 A | 1/2000 | Egres, Jr. |
| 6,051,015 A | 4/2000 | Maahs |
| 6,086,600 A | 7/2000 | Kortenbach |
| 6,098,629 A | 8/2000 | Johnson et al. |
| 6,102,922 A | 8/2000 | Jakobsson et al. |
| 6,113,609 A | 9/2000 | Adams |
| 6,120,534 A | 9/2000 | Ruiz |
| 6,126,058 A | 10/2000 | Adams et al. |
| 6,146,416 A | 11/2000 | Andersen et al. |
| 6,159,146 A | 12/2000 | El Gazayerli |
| 6,159,238 A | 12/2000 | Killion et al. |
| 6,197,022 B1 | 3/2001 | Baker |
| 6,206,930 B1 | 3/2001 | Burg et al. |
| 6,245,088 B1 | 6/2001 | Lowery |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,287,334 B1 | 9/2001 | Moll et al. |
| 6,302,917 B1 | 10/2001 | Dua et al. |
| 6,358,197 B1 | 3/2002 | Silverman et al. |
| 6,416,522 B1 | 7/2002 | Strecker |
| 6,425,916 B1 | 7/2002 | Garrison et al. |
| 6,454,785 B2 | 9/2002 | De Hoyos Garza et al. |
| 6,460,543 B1 | 10/2002 | Forsell |
| 6,461,366 B1 | 10/2002 | Seguin |
| 6,494,888 B1 | 12/2002 | Laufer et al. |
| 6,494,895 B2 | 12/2002 | Addis |
| 6,503,264 B1 | 1/2003 | Birk |
| 6,506,196 B1 | 1/2003 | Laufer |
| 6,527,784 B2 | 3/2003 | Adams et al. |
| 6,540,789 B1 | 4/2003 | Silverman et al. |

(56) References Cited

U.S. PATENT DOCUMENTS

| | | |
|---|---|---|
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor |
| 6,572,627 B2 | 6/2003 | Gabbay |
| 6,572,629 B2 | 6/2003 | Kalloo et al. |
| 6,575,896 B2 | 6/2003 | Silverman et al. |
| 6,592,596 B1 | 7/2003 | Geitz |
| 6,596,023 B1 | 7/2003 | Nunez et al. |
| 6,607,555 B2 | 8/2003 | Patterson et al. |
| 6,627,206 B2 | 9/2003 | Lloyd |
| 6,632,227 B2 | 10/2003 | Adams |
| 6,663,639 B1 | 12/2003 | Laufer et al. |
| 6,675,809 B2 | 1/2004 | Stack et al. |
| 6,733,512 B2 | 5/2004 | McGhan |
| 6,740,098 B2 | 5/2004 | Abrams et al. |
| 6,740,121 B2 | 5/2004 | Geitz |
| 6,746,460 B2 | 6/2004 | Gannoe et al. |
| 6,755,869 B2 | 6/2004 | Geitz |
| 6,764,518 B2 | 7/2004 | Godin |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,821,285 B2 | 11/2004 | Laufer et al. |
| 6,835,200 B2 | 12/2004 | Laufer et al. |
| 6,845,776 B2 | 1/2005 | Stack et al. |
| 6,916,332 B2 | 7/2005 | Adams |
| 6,932,838 B2 | 8/2005 | Schwartz et al. |
| 6,960,233 B1 | 11/2005 | Berg et al. |
| 6,966,875 B1 | 11/2005 | Longobardi |
| 6,981,978 B2 | 1/2006 | Gannoe |
| 6,981,980 B2 | 1/2006 | Sampson et al. |
| 6,994,715 B2 | 2/2006 | Gannoe et al. |
| 7,011,094 B2 | 3/2006 | Rapacki et al. |
| 7,020,531 B1 | 3/2006 | Colliou et al. |
| 7,025,791 B2 | 4/2006 | Levine et al. |
| 7,033,373 B2 | 4/2006 | De La Torre et al. |
| 7,033,384 B2 | 4/2006 | Gannoe et al. |
| 7,037,344 B2 | 5/2006 | Kagan et al. |
| 7,056,305 B2 | 6/2006 | Garza |
| 7,066,945 B2 | 6/2006 | Hashiba et al. |
| 7,083,629 B2 | 8/2006 | Weller et al. |
| 7,090,699 B2 | 8/2006 | Geitz |
| 7,097,650 B2 | 8/2006 | Weller et al. |
| 7,097,665 B2 | 8/2006 | Stack et al. |
| 7,111,627 B2 | 9/2006 | Stack et al. |
| 7,112,186 B2 | 9/2006 | Shah |
| 7,120,498 B2 | 10/2006 | Imran et al. |
| 7,121,283 B2 | 10/2006 | Stack et al. |
| 7,146,984 B2 | 12/2006 | Stack et al. |
| 7,147,140 B2 | 12/2006 | Wukusick et al. |
| 7,152,607 B2 | 12/2006 | Stack et al. |
| 7,160,296 B2 | 1/2007 | Pearson et al. |
| 7,160,312 B2 | 1/2007 | Saadat |
| 7,172,613 B2 | 2/2007 | Wazne |
| 7,175,638 B2 | 2/2007 | Gannoe et al. |
| 7,175,660 B2 | 2/2007 | Cartledge et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,229,453 B2 | 6/2007 | Anderson et al. |
| 7,255,675 B2 | 8/2007 | Gertner et al. |
| 7,261,722 B2 | 8/2007 | McGuckin, Jr. et al. |
| 7,288,101 B2 | 10/2007 | Deem et al. |
| 7,306,614 B2 | 12/2007 | Weller et al. |
| 7,315,509 B2 | 1/2008 | Jeong et al. |
| 7,316,716 B2 | 1/2008 | Egan |
| 7,320,696 B2 | 1/2008 | Gazi et al. |
| 7,326,207 B2 | 2/2008 | Edwards |
| 7,335,210 B2 | 2/2008 | Smit |
| 7,347,863 B2 | 3/2008 | Rothe et al. |
| 7,347,875 B2 | 3/2008 | Levine et al. |
| 7,354,454 B2 | 4/2008 | Stack et al. |
| 7,399,304 B2 | 7/2008 | Gambale et al. |
| 7,431,725 B2 | 10/2008 | Stack et al. |
| 7,461,767 B2 | 12/2008 | Viola et al. |
| 7,470,251 B2 | 12/2008 | Shah |
| 7,485,142 B2 | 2/2009 | Milo |
| 7,503,922 B2 | 3/2009 | Deem et al. |
| 7,520,884 B2 | 4/2009 | Swanstrom et al. |
| 7,575,586 B2 | 8/2009 | Berg et al. |
| 7,608,114 B2 | 10/2009 | Levine et al. |
| 7,615,064 B2 | 11/2009 | Bjerken |
| 7,625,371 B2 | 12/2009 | Morris et al. |
| 7,628,821 B2 | 12/2009 | Stack et al. |
| 7,662,161 B2 | 2/2010 | Briganti et al. |
| 7,670,279 B2 | 3/2010 | Gertner |
| 7,674,721 B2 | 3/2010 | Usami |
| 7,695,446 B2 | 4/2010 | Levine et al. |
| 7,699,863 B2 | 4/2010 | Marco et al. |
| 7,708,181 B2 | 5/2010 | Cole et al. |
| 7,717,843 B2 | 5/2010 | Balbierz et al. |
| 7,721,932 B2 | 5/2010 | Cole et al. |
| 7,731,757 B2 | 6/2010 | Taylor et al. |
| 7,744,613 B2 | 6/2010 | Ewers et al. |
| 7,744,627 B2 | 6/2010 | Orban, III et al. |
| 7,753,870 B2 | 7/2010 | Demarais et al. |
| 7,766,861 B2 | 8/2010 | Levine et al. |
| 7,819,836 B2 | 10/2010 | Levine et al. |
| 7,846,138 B2 | 12/2010 | Dann et al. |
| 7,846,174 B2 | 12/2010 | Baker et al. |
| 7,881,797 B2 | 2/2011 | Griffin et al. |
| 7,892,214 B2 | 2/2011 | Kagan et al. |
| 7,892,292 B2 | 2/2011 | Stack et al. |
| 7,934,631 B2 | 5/2011 | Balbierz et al. |
| 7,954,683 B1 | 6/2011 | Knodel et al. |
| 8,020,741 B2 | 9/2011 | Cole et al. |
| 8,469,977 B2 | 6/2013 | Balbierz et al. |
| 8,747,421 B2 | 6/2014 | Balbierz et al. |
| 8,763,876 B2 | 7/2014 | Kostrzewski |
| 9,022,274 B2 | 5/2015 | Penna |
| 9,033,204 B2 | 5/2015 | Shelton, IV et al. |
| 9,113,866 B2 | 8/2015 | Felder et al. |
| 9,216,019 B2 | 12/2015 | Schmid et al. |
| 9,282,974 B2 | 3/2016 | Shelton, IV |
| 9,451,956 B2 * | 9/2016 | Balbierz ............ A61B 17/068 |
| 2001/0011543 A1 | 8/2001 | Forsell |
| 2001/0044595 A1 | 11/2001 | Reydel et al. |
| 2002/0082621 A1 | 6/2002 | Schurr et al. |
| 2002/0188354 A1 | 12/2002 | Peghini |
| 2003/0191525 A1 | 10/2003 | Thornton |
| 2003/0199990 A1 | 10/2003 | Stack et al. |
| 2003/0199991 A1 | 10/2003 | Stack et al. |
| 2003/0220660 A1 | 11/2003 | Kortenbach et al. |
| 2004/0044364 A1 | 3/2004 | DeVries et al. |
| 2004/0068726 A1 | 4/2004 | Levy et al. |
| 2004/0092892 A1 | 5/2004 | Kagan et al. |
| 2004/0098043 A1 | 5/2004 | Trout |
| 2004/0117031 A1 | 6/2004 | Stack et al. |
| 2004/0133219 A1 | 7/2004 | Forsell |
| 2004/0138761 A1 | 7/2004 | Stack et al. |
| 2004/0143342 A1 | 7/2004 | Stack et al. |
| 2004/0162568 A1 | 8/2004 | Saadat et al. |
| 2004/0215216 A1 | 10/2004 | Gannoe et al. |
| 2004/0220682 A1 | 11/2004 | Levine et al. |
| 2004/0225183 A1 | 11/2004 | Michlitsch et al. |
| 2004/0243223 A1 | 12/2004 | Kraemer et al. |
| 2005/0004430 A1 | 1/2005 | Lee et al. |
| 2005/0049718 A1 | 3/2005 | Dann et al. |
| 2005/0075654 A1 | 4/2005 | Kelleher |
| 2005/0080444 A1 | 4/2005 | Kraemer et al. |
| 2005/0085787 A1 | 4/2005 | Laufer |
| 2005/0096750 A1 | 5/2005 | Kagan et al. |
| 2005/0159769 A1 | 7/2005 | Alverdy |
| 2005/0177181 A1 | 8/2005 | Kagan et al. |
| 2005/0192599 A1 | 9/2005 | Demarais |
| 2005/0192615 A1 | 9/2005 | Torre et al. |
| 2005/0247320 A1 | 11/2005 | Stack et al. |
| 2005/0251158 A1 | 11/2005 | Saadat et al. |
| 2005/0256533 A1 | 11/2005 | Roth et al. |

(56) References Cited

U.S. PATENT DOCUMENTS

| | | |
|---|---|---|
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0015006 A1 | 1/2006 | Laurence et al. |
| 2006/0020278 A1 | 1/2006 | Burnett et al. |
| 2006/0058829 A1 | 3/2006 | Sampson et al. |
| 2006/0151568 A1 | 7/2006 | Weller et al. |
| 2006/0155259 A1 | 7/2006 | Maclay |
| 2006/0155311 A1 | 7/2006 | Hashiba et al. |
| 2006/0178560 A1 | 8/2006 | Saadat et al. |
| 2006/0178691 A1 | 8/2006 | Binmoeller |
| 2006/0195139 A1 | 8/2006 | Gertner |
| 2006/0253142 A1 | 11/2006 | Bjerken et al. |
| 2006/0271076 A1 | 11/2006 | Weller et al. |
| 2006/0282095 A1 | 12/2006 | Stokes et al. |
| 2007/0010864 A1 | 1/2007 | Dann et al. |
| 2007/0032800 A1 | 2/2007 | Ortiz et al. |
| 2007/0043384 A1 | 2/2007 | Ortiz et al. |
| 2007/0055292 A1 | 3/2007 | Ortiz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0208360 A1 | 9/2007 | Demarais et al. |
| 2007/0219571 A1 | 9/2007 | Balbierz et al. |
| 2007/0239284 A1 | 10/2007 | Skerven et al. |
| 2007/0260327 A1 | 11/2007 | Case et al. |
| 2007/0276428 A1 | 11/2007 | Haller et al. |
| 2007/0276432 A1 | 11/2007 | Stack et al. |
| 2008/0033574 A1 | 2/2008 | Bessler et al. |
| 2008/0065122 A1 | 3/2008 | Stack et al. |
| 2008/0097510 A1 | 4/2008 | Albrecht et al. |
| 2008/0116244 A1 | 5/2008 | Rethy et al. |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0208356 A1 | 8/2008 | Stack et al. |
| 2008/0269797 A1 | 10/2008 | Stack et al. |
| 2008/0272175 A1 | 11/2008 | Holsten et al. |
| 2008/0294179 A1 | 11/2008 | Balbierz et al. |
| 2008/0319471 A1 | 12/2008 | Sosnowski et al. |
| 2009/0018558 A1 | 1/2009 | Laufer et al. |
| 2009/0024143 A1 | 1/2009 | Crews et al. |
| 2009/0030284 A1 | 1/2009 | Cole et al. |
| 2009/0125040 A1 | 5/2009 | Hambly et al. |
| 2009/0171383 A1 | 7/2009 | Cole et al. |
| 2009/0177215 A1 | 7/2009 | Stack et al. |
| 2009/0182424 A1 | 7/2009 | Marco et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236396 A1 | 9/2009 | Cole et al. |
| 2009/0236397 A1 | 9/2009 | Cole et al. |
| 2009/0236398 A1 | 9/2009 | Cole et al. |
| 2009/0236400 A1 | 9/2009 | Cole et al. |
| 2009/0236401 A1 | 9/2009 | Cole et al. |
| 2009/0299487 A1 | 12/2009 | Stack et al. |
| 2010/0016988 A1 | 1/2010 | Stack et al. |
| 2010/0100109 A1 | 4/2010 | Stack et al. |
| 2010/0204719 A1 | 8/2010 | Balbierz et al. |
| 2011/0192881 A1 | 8/2011 | Balbierz et al. |

FOREIGN PATENT DOCUMENTS

| | | |
|---|---|---|
| DE | 8708978 U1 | 11/1987 |
| EP | 0775471 A1 | 5/1997 |
| EP | 1256318 A1 | 11/2002 |
| EP | 1492478 A1 | 1/2005 |
| EP | 1602336 A2 | 12/2005 |
| FR | 2768324 A1 | 3/1999 |
| JP | H09168597 A | 6/1997 |
| JP | 2005-160933 | 6/2005 |
| WO | WO-9101117 A1 | 2/1991 |
| WO | WO-9525468 A1 | 9/1995 |
| WO | WO-9747231 A2 | 12/1997 |
| WO | WO-0012027 A1 | 3/2000 |
| WO | WO-0032137 A1 | 6/2000 |
| WO | WO-0078227 A1 | 12/2000 |
| WO | WO-0141671 A2 | 6/2001 |
| WO | WO-0145485 A2 | 6/2001 |
| WO | WO-0149359 A1 | 7/2001 |
| WO | WO-0166018 A1 | 9/2001 |
| WO | WO-0185034 A1 | 11/2001 |
| WO | WO-0189393 A1 | 11/2001 |
| WO | WO-02060328 A1 | 8/2002 |
| WO | WO-03017882 A2 | 3/2003 |
| WO | WO-03086246 A1 | 10/2003 |
| WO | WO-03086247 A1 | 10/2003 |
| WO | WO-03090633 A2 | 11/2003 |
| WO | WO-03094784 A2 | 11/2003 |
| WO | WO-03094785 A1 | 11/2003 |
| WO | WO-03099137 A2 | 12/2003 |
| WO | WO-03105698 A2 | 12/2003 |
| WO | WO-2004019765 A2 | 3/2004 |
| WO | WO-2004019787 A2 | 3/2004 |
| WO | WO-2004032760 A2 | 4/2004 |
| WO | WO-2004037064 A2 | 5/2004 |
| WO | WO-2004041133 A1 | 5/2004 |
| WO | WO-2004064680 A1 | 8/2004 |
| WO | WO-2004064685 A1 | 8/2004 |
| WO | WO-2004080336 A2 | 9/2004 |
| WO | WO-2004110285 A1 | 12/2004 |
| WO | WO-2005037152 A1 | 4/2005 |
| WO | WO-2005079673 A2 | 9/2005 |
| WO | WO-2005096991 A1 | 10/2005 |
| WO | WO-2005105003 A1 | 11/2005 |
| WO | WO-2006016894 A1 | 2/2006 |
| WO | WO-2006055365 A2 | 5/2006 |
| WO | WO-2006081174 A2 | 8/2006 |
| WO | WO-2006081174 A3 | 8/2006 |
| WO | WO-2006127593 A2 | 11/2006 |
| WO | WO-2007041598 A1 | 4/2007 |
| WO | WO-2008030403 A1 | 3/2008 |
| WO | WO-2008033409 A1 | 3/2008 |
| WO | WO-2008033474 A2 | 3/2008 |
| WO | WO-2008141288 A1 | 11/2008 |
| WO | WO-2009011881 A1 | 1/2009 |
| WO | WO-2009011882 A2 | 1/2009 |
| WO | WO-2009086549 A1 | 7/2009 |
| WO | WO-2009117533 A2 | 9/2009 |
| WO | WO-2010054399 A1 | 5/2010 |
| WO | WO-2010054404 A1 | 5/2010 |

OTHER PUBLICATIONS

International Search Report and Written Opinion for Application No. PCT/US2008/008726, dated Oct. 16, 2008, 13 pages.
International Search Report for Application No. PCT/US2002/027177, dated Feb. 14, 2003, 5 pages.
International Search Report for Application No. PCT/US2003/004378, dated Aug. 13, 2003, 4 pages.
International Search Report for Application No. PCT/US2003/004449, dated Aug. 13, 2003, 4 pages.
International Search Report for Application No. PCT/US2003/033605, dated Mar. 29, 2004, 4 pages.
International Search Report for Application No. PCT/US2003/033606, dated Mar. 29, 2004, 6 pages.
International Search Report for Application No. PCT/US2004/006695, dated Sep. 8, 2004, 6 pages.
International Search Report for Application No. PCT/US2004/033007, dated Feb. 9, 2005, 6 pages.
International Search Report for Application No. PCT/US2005/014372, dated Jul. 28, 2005, 1 page.
International Search Report for Application No. PCT/US2006/019727, dated Apr. 19, 2007, 3 pages.
International Search Report for Application No. PCT/US2006/038684, dated Feb. 14, 2007, 4 pages.
International Search Report for Application No. PCT/US2007/019227, dated Feb. 20, 2008, 4 pages.

(56) References Cited

OTHER PUBLICATIONS

International Search Report for Application No. PCT/US2007/019833, dated Feb. 20, 2008, 5 pages.
International Search Report for Application No. PCT/US2007/019940, dated Mar. 14, 2008, 3 pages.
International Search Report for Application No. PCT/US2008/008729, dated Aug. 18, 2009, 6 pages.
International Search Report for Application No. PCT/US2008/063440, dated Aug. 1, 2008, 5 pages.
International Search Report for Application No. PCT/US2008/088581, dated Feb. 26, 2009, 2 pages.
International Search Report for Application No. PCT/US2009/037586, dated Sep. 28, 2009, 4 pages.
International Search Report for Application No. PCT/US2009/063925, dated Jan. 12, 2010, 1 page.
International Search Report for Application No. PCT/US2009/063930, dated Jan. 12, 2010, 1 page.
Extended European Search Report dated Mar. 14, 2014 issued in PCT Appln. No. PCT/US2009063930, (13 pages).
Stecco, et al., "Safety of a Gastric Restrictive Implant in a Canine Model," Stecco Group, 2004, San Jose and Barosense, Inc., Redwood City, California.
Stecco, et al., "Trans-oral Plication Formation and Gastric Implant Placement in a Canine Model," Stecco Group, 2004, San Jose and Barosense, Inc., Redwood City, California.

\* cited by examiner

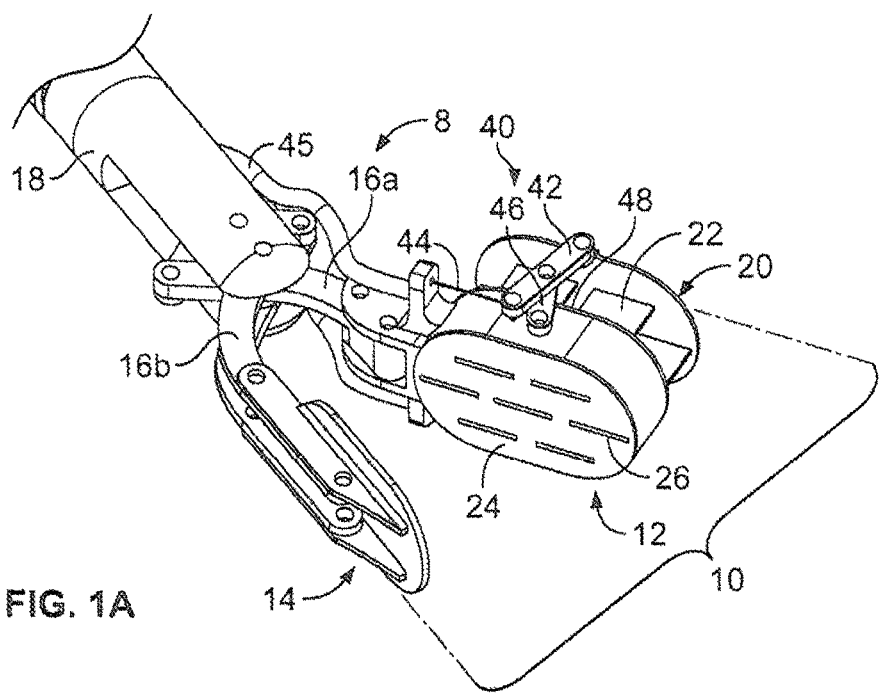
FIG. 1A
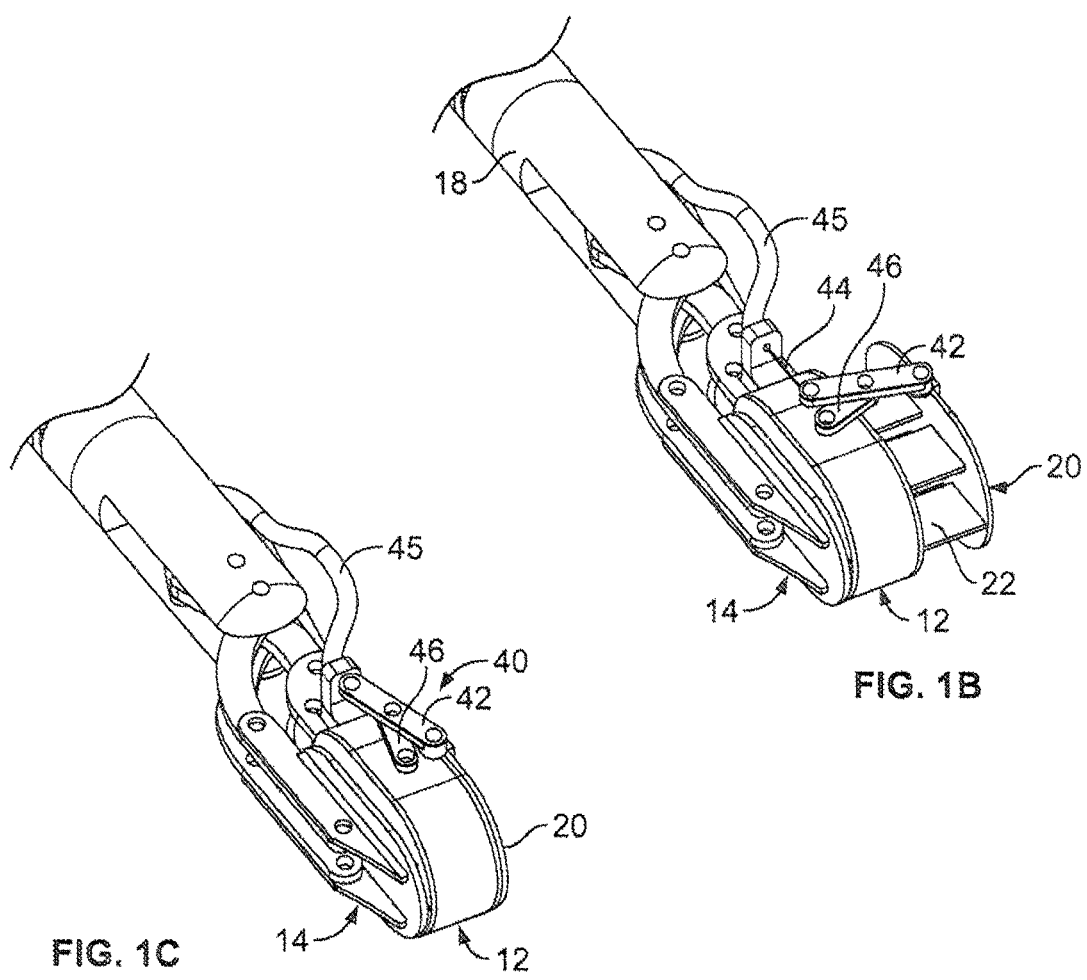
FIG. 1B
FIG. 1C

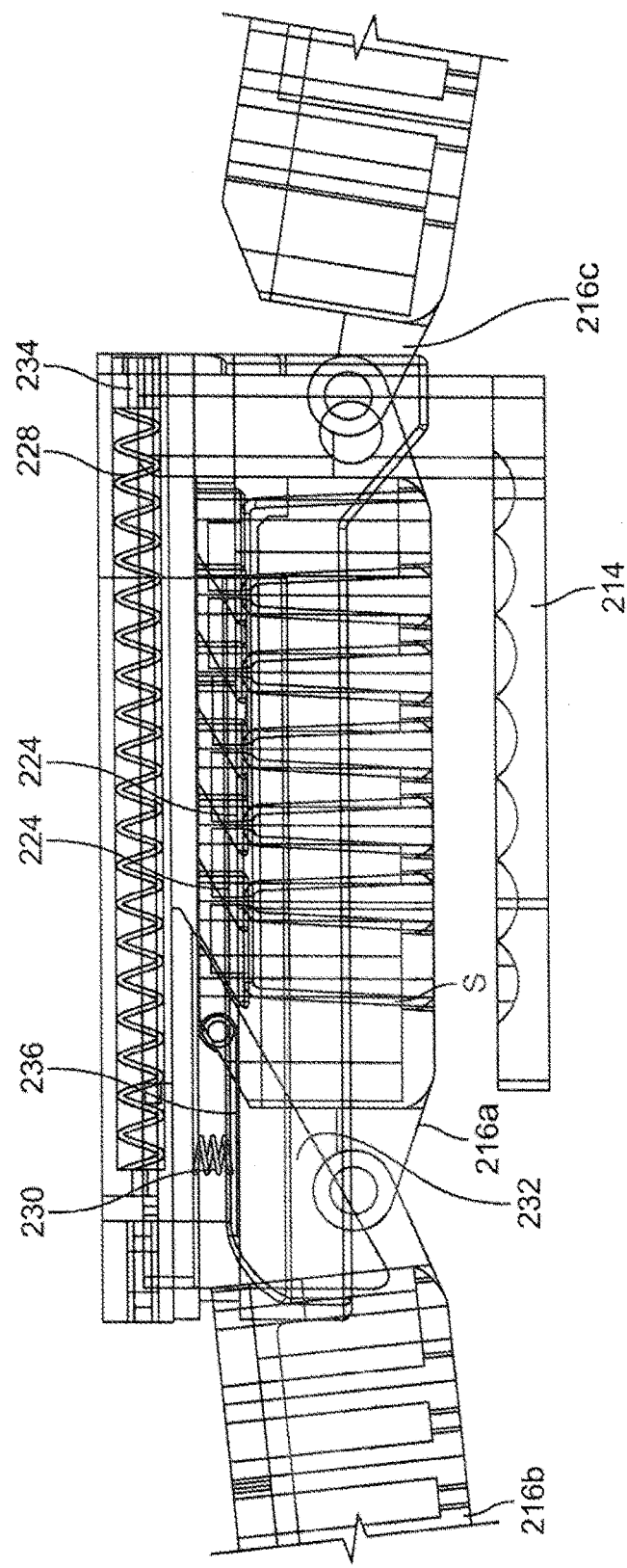

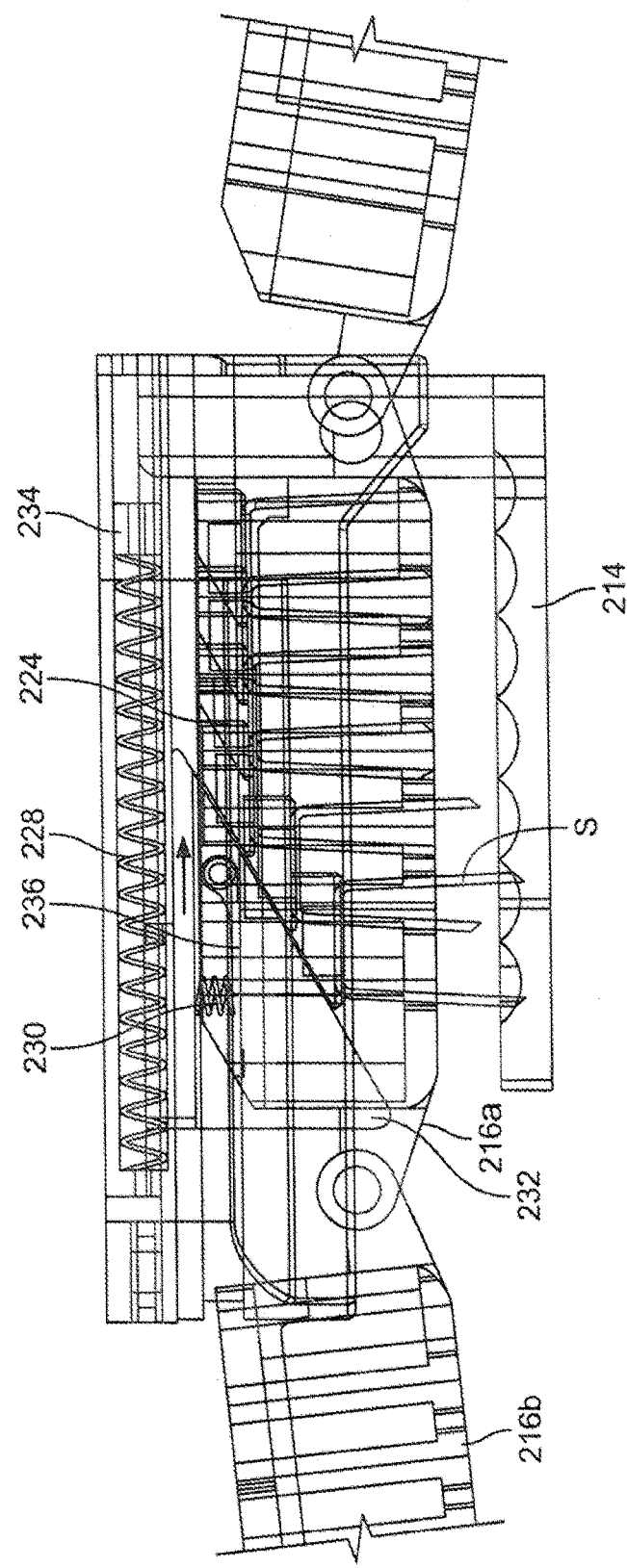

MULTI-FIRE STAPLING METHODS

PRIORITY

This application is a continuation of U.S. patent application Ser. No. 14/259,781, filed on Apr. 23, 2014, (now U.S. Pat. No. 9,451,956, issued on Sep. 27, 2016) which is a continuation of U.S. patent application Ser. No. 13/089,216, filed on Apr. 18, 2011 (now U.S. Pat. No. 8,747,421, issued on Jun. 10, 2014), which is a divisional of U.S. patent application Ser. No. 12/268,404, filed on Nov. 10, 2008 (now U.S. Pat. No. 7,934,631, issued on May 3, 2011). Each of the above-referenced applications is incorporated herein by reference in its entirety.

TECHNICAL FIELD OF THE INVENTION

The present invention relates generally to the field of medical staplers. More specifically, the present invention relates to the field of self-reloading staplers.

BACKGROUND

Surgical staplers have been in clinical use for many years. They have become a standard tool used by surgeons in procedures requiring tissue apposition, ligation, resection and/or anastomosis. Staplers reduce overall procedure time by eliminating the need for the time-consuming placement of sutures. Staplers can reduce blood loss in certain procedures involving resection of tissue to be stapled, by allowing tissue cutting/resection to be performed after the tissue is compressed and stapled. For example, a pair of staple rows is first formed, and then the tissue is cut along a line between the staple rows.

Surgical staplers are configured to fire the multiple staples of a staple array (e.g. a linear array such as a staple line, a circular array etc.) in a single shot. Early staplers comprised reusable handles and disposable staple cartridge loads holding a single staple array. Subsequent staplers used disposable handles and disposable cartridge loads. During clinical use of the prior art staplers, spent cartridges must be removed from the handles and replaced with fresh cartridges. Thus, a stapler carrying a single charge of staples is fired into the tissue and then removed from the patient. The spent cartridge is ejected and a new cartridge is loaded for the next staple line. The stapler is reintroduced into the body and the process is repeated for the next line or array of staples to be applied to tissue. The need for constant reloading of the stapler is particularly time consuming in transoral natural orifice surgeries, as the time required for repositioning the stapler head after removing the device from the stomach or other body cavity is not insignificant. Moreover, the requirement for multiple staple cartridges per procedure adds to the overall cost of the procedure.

Disclosed herein is a staple housing or cartridge preloaded with at least two sets of staples such that at least two staple arrays can be applied to tissue before the stapler must be actively reloaded. Each staple set contains two or more staples, with the staple sets arranged to form a staple array of at least two (but preferably more) staples in a linear or non-linear array. Each staple housing or cartridge is pre-loaded with at least two staple sets, but three, four, or more staples sets may instead be provided in the staple housing to limit the number of times the staple housing must be reloaded or equipped with a new cartridge during the course of a procedure.

The disclosed multi-fire staple housings and cartridges are suitable for use in any form of medical stapling procedure, including endoscopic, laparoscopic, open surgical and natural orifice procedures which utilize natural body orifices for surgery to reduce the invasiveness of these procedures. Natural orifices include, but are not limited to the esophagus, anus and vagina.

The disclosed multi-fire staple housings and cartridges are particularly beneficial for use within the stomach, such as during stomach partitioning procedures in which the stomach is partitioned from the inside by connecting tissue within the stomach (see commonly owned application Ser. No. 12/119,329, filed May 12, 2008, entitled DEVICES AND METHODS FOR STOMACH PARTITIONING), or for forming tissue plications within the stomach for use in retaining stomach implants (see commonly owned application Ser. No. 12/175,242, filed Jul. 17, 2008, entitled ENDOSCOPIC IMPLANT SYSTEM AND METHOD and application Ser. No. 12/050,169, filed Mar. 18, 2008, entitled ENDOSCOPIC STAPLING DEVICES AND METHODS).

Multi-fire staple housings or cartridges may be incorporated into multi-function devices, such as those that perform both stapling and cutting (e.g. end to end anastomosis devices, or linear stapling/cutting devices), and/or those that can both acquire and staple tissue. The staple housing is a removable/replaceable cartridge or magazine and/or it may be refillable by inserting additional staples into it. In other embodiments, the staple holder may be neither replaceable nor refillable.

BRIEF DESCRIPTION OF THE DRAWINGS

FIG. 1A is a perspective view of a first embodiment of a multi-fire stapler head, showing the jaws in the open position and the staple driver in the pre-firing position.

FIG. 1B is similar to FIG. 1A and shows the jaws in the closed position and the staple driver in the pre-firing position.

FIG. 1C is similar to FIG. 1A and shows the jaws in the closed position and the staple driver in the firing position.

FIGS. 13 through 15 are a sequence of steps illustrating use of the stapler of FIG. 1A, in which FIG. 13 is a side elevation view showing the jaws closed and the staple driver in the retracted position, FIG. 14 is a side elevation view showing the jaws opened and the staple driver in the retracted position, and FIG. 15 is a side elevation view showing the jaws closed and the stapler driver extending through the staple housing to drive an array of staples.

FIGS. 26A through 26E are a sequence of drawings illustrating the steps of driving staples from a cartridge, and the advancement of a second cartridge into the staple housing.

DETAILED DESCRIPTION

Figure 2:
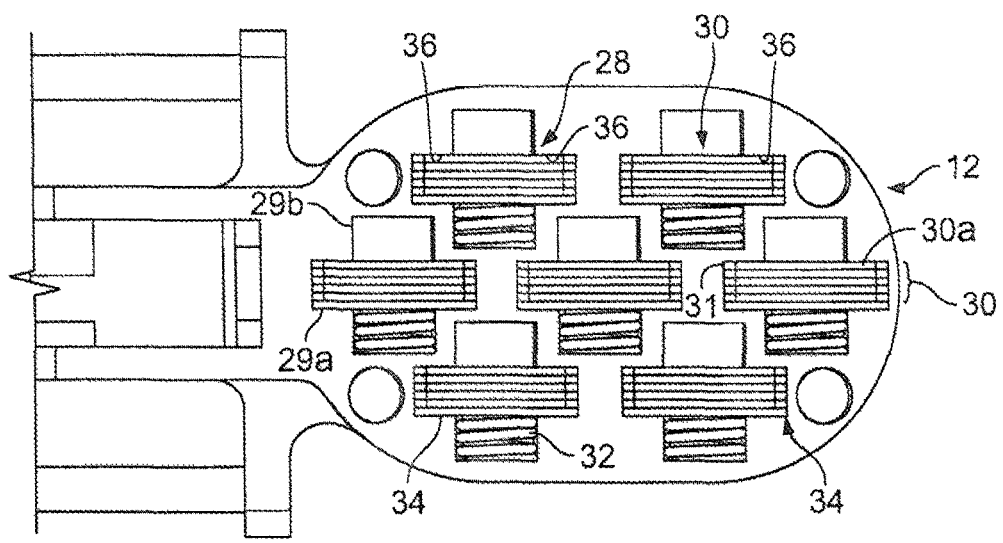
FIG. 2 is a plan view of the stapler housing, with the face plate removed.

FIG. 1A generally shows a stapler 8 employing a multi-fire staple head 10. Staple head 10 includes a staple housing 12 and a corresponding anvil 14 carried by opposed jaw members 16a, 16b on the distal portion of an elongate shaft 18. As will be evident from the description that follows, the staple housing 12 has an array of staples each in a staple delivery location or "ready position" ready to be fired into target tissue. A staple driver 20 is positioned for advancement from the position shown in FIG. 1B to the position shown in FIG. 1C so as to drive the ready-position staples from the staple head 12 into the tissue using staple pushers 22. During use, the staples in the ready positions are fired into the target tissue using the staple pushers 22. After the array has been fired, feed mechanisms within the staple housing advance a second array of staples from one or more staple storage locations into the ready positions in preparation for firing of the second array.

Referring again to FIG. 1A, staple head 12 includes a face plate 24 having a number of openings 26 through which the staples exit the staple head 12 during stapling. The openings 26 are thus arranged in the pattern of the desired staple array. An internal feed mechanism within the staple housing 12 functions to feed staples from stacks of staples into ready positions, which are aligned with the openings 26. In the illustrated embodiments, separate feed mechanisms are used to move each staple of the array into its corresponding ready position. Other embodiments, however, may use feed mechanisms capable of feeding staples into multiple ready positions. FIG. 2 shows a plan view of the staple housing 12 in which the face plate 24 has been removed to reveal the feed mechanisms used to feed staples into ready positions. As shown, the staple housing 12 includes a plurality of cells 28, the number of which corresponds to the number of staples in the array. Any number of shapes may be used for the cells 28, although in the illustrated embodiment, each cell 28 includes an intermediate section 29a and narrower end sections 29b.

Each cell 28 contains a collection or stack 30 of staples disposed in the intermediate section 29a. One of the staples 30a is in a ready position 31 aligned with the corresponding opening 26 (FIG. 1A) of the overlying faceplate 24. In one of the end sections 29b is a feed mechanism which includes at least one spring 32 and a plate 34. As shown, one end of the spring 32 contacts a wall in the cell 28, and the other end contacts one face of the plate 34. The opposite face of the plate 34 is in contact with staple stack 30. The spring force against the plate 34 biases the end-most staple 30a in the ready position 31, in contact with the walls 36. When a staple is advanced from the ready position into tissue, this spring force advances the stack's next staple into the ready position 31.

Figure 3A:
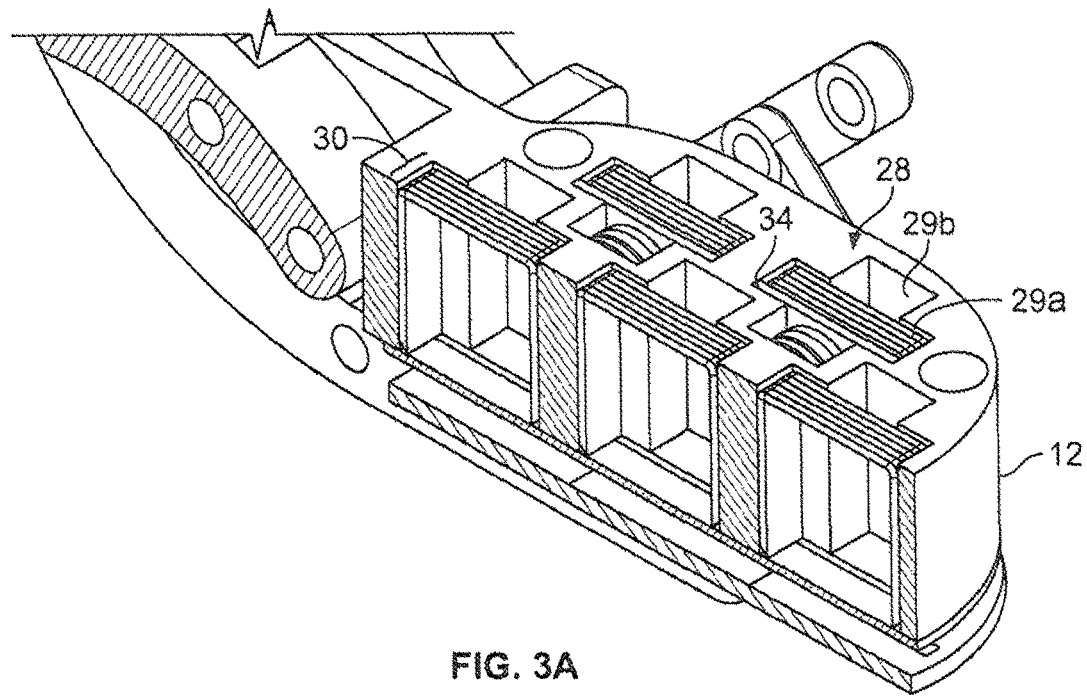
FIG. 3A is a perspective view showing a longitudinal cross-section of the staple housing with the back plate removed.
Figure 3B:
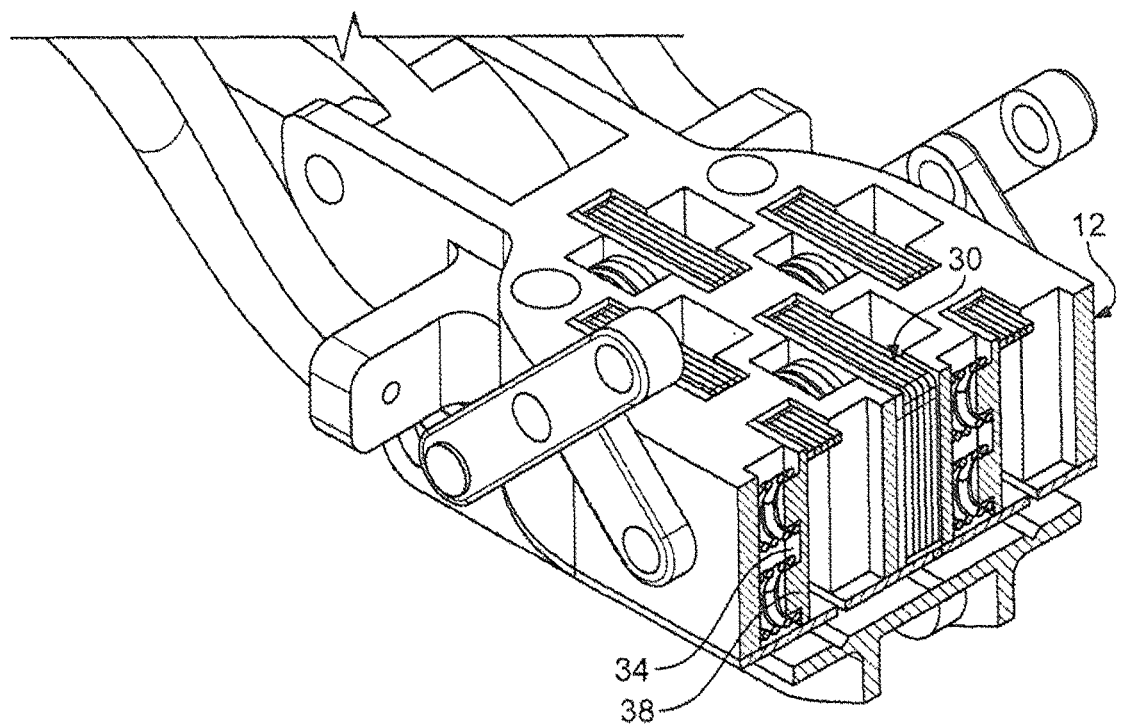
FIG. 3B is a perspective view showing a lateral cross-section of the staple housing with the back plate removed.
Figure 4:
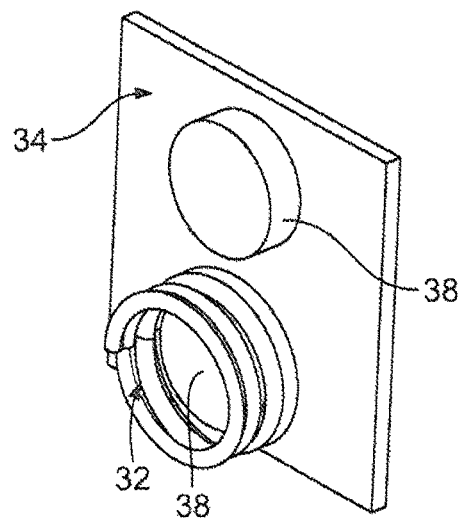
FIG. 4 is a perspective view of the staple advancing plate and one of the two springs provided on the plate.

Various types of springs may be used in the feed mechanism. In the embodiment illustrated in FIGS. 2-3B, a pair of compression springs 32 is used within each cell 28. As shown in FIG. 4, each spring 32 may be supported on one end by a protrusion or button 38 on the plate 34.

Figure 5A:
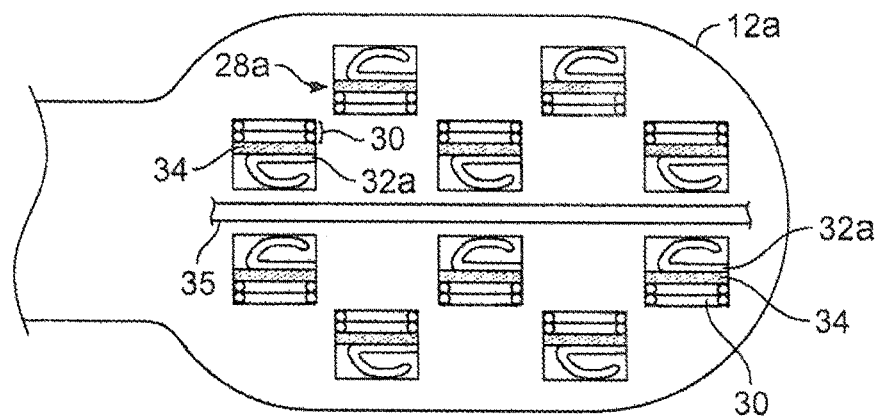
FIG. 5A is similar to FIG. 2 but shows an alternate type of spring in the feed mechanism.
Figure 5B:
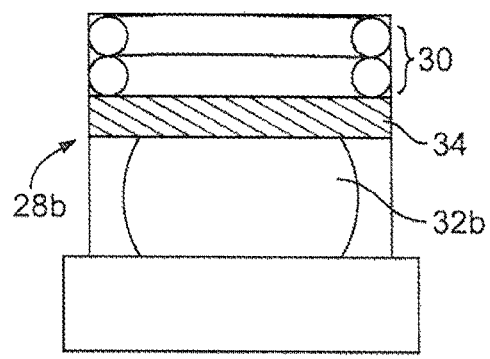
FIG. 5B shows a single cell of the embodiment of FIG. 5A, with the spring replaced by an elastomeric member.

In alternate spring arrangements, the compression springs are replaced by one or more leaf springs 32a as shown in FIG. 5A and/or by one or more elastomeric spring elements 32b as shown in FIG. 5B. It should also be noted that FIG. 5A illustrates the staple stacks and feed mechanisms in a staple housing having a channel 35 through which a cutting blade can pass for tissue resection subsequent to stapling.

Figure 6:
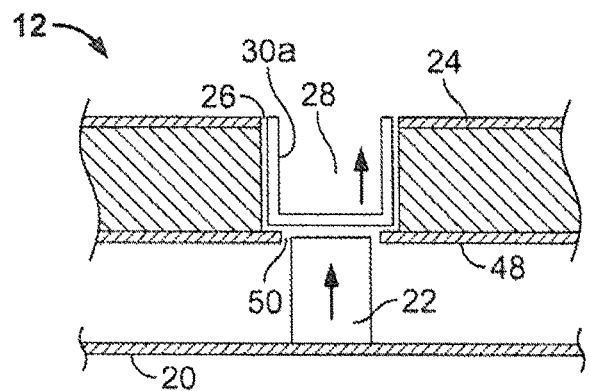
FIG. 6 shows a cross-section view of a portion of the staple housing and a portion of the staple driver in the region of a single one of the cells.

FIG. 6 is a cross-section view of a single cell and surrounding region of the staple housing 12. This figure illustrates that a back plate 48 is positioned on the opposite side of the staple housing 12 from the face plate 24, and includes openings 50 (only one of which is shown) aligned with the corresponding openings 26 (one shown) on the face plate 24. The openings 50 are positioned to permit a staple pusher to pass through them into the staple housing 12 to drive staples out the openings 26 in the face plate 24.

Features used to push staples from the ready position through the tissue will next be described. Referring to FIG. 1A, staple driver 20 includes a plurality of staple pushers 22 extending from a plate. A linkage 40 couples the staple driver 20 to the stapler head 12, with the staple pushers 22 aligned with openings 50 in the back plate 48 (FIG. 6).

Linkage 40 has a first link 42 having a first end pivotally coupled to the plate of the staple pusher 22 and a second end connected to a pull cable 44. Pull cable 44 extends through a cable housing 45 to a handle on the shaft. A second link 46 is pivotably coupled at one end to an intermediate section of the first link 42, and it is pivotably coupled at its other end to the staple housing 12. The linkage is configured such that application of tension to the pull cable 44 pivots the links 42, 46 from the position shown in FIG. 1B to that shown in FIG. 1C, thus driving the staple driver 20 towards the staple housing, causing staple pushers 22 to pass into the staple housing 12 and to drive the staples in the manner illustrated in FIG. 6.

Various other methods may be used to advance a staple pusher to drive a staple from the staple housing. Some alternate methods, each of which uses a translating staple driver, are shown schematically in FIGS. 7A through 9E.

Figure 7A:
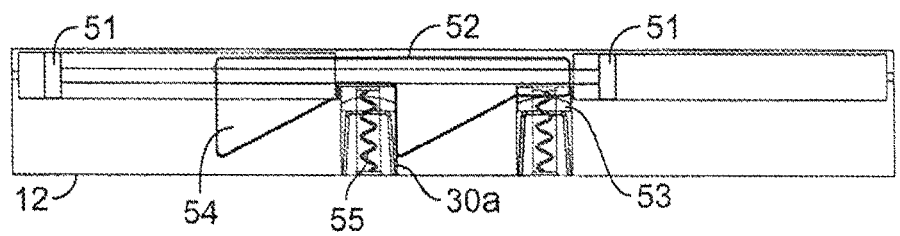
FIGS. 7A-7C are a sequence of side elevation views schematically illustrating movement of an alternative staple driver to drive staples from a staple housing into tissue.
Figure 7B:
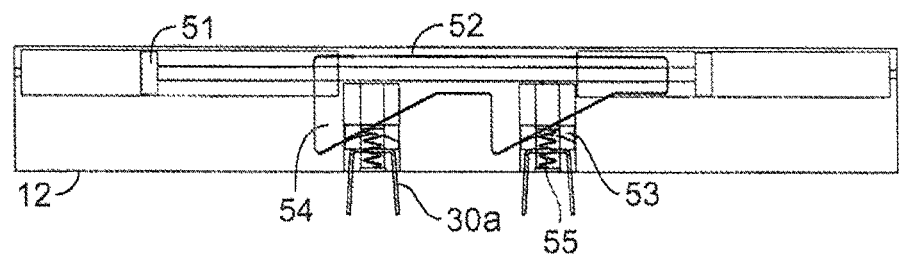
Figure 7C:
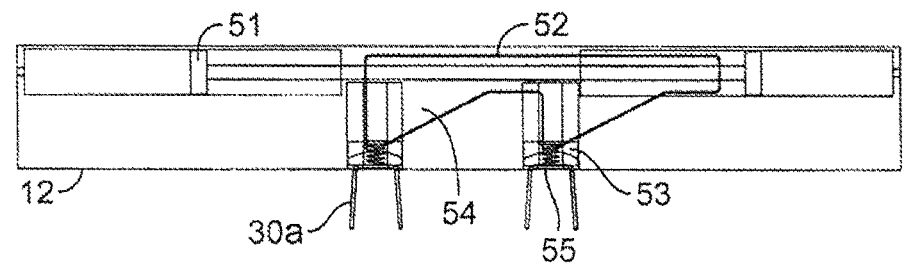

FIGS. 7A-7C illustrate a linear arrangement of staples 30a being driven from a staple housing 12 (which could be a cartridge or magazine) with a driver 52 moveable in a direction parallel to the back span of the staples. This motion could be generated with hydraulic pistons 51 as shown, or with pull cables, linkages, rotary input, as well as other means. Pushers 53 are positioned in contact with the back spans of the staples. The driver 52 includes a plurality of wedge elements 54 positioned such that as the driver is advanced, the sloped edges of the wedge elements 54 contact the pushers 53, causing the pushers to drive the staples 30a from their corresponding chambers in the staple housing (FIGS. 7B and 7C. In a modification of this embodiment, the pusher 53 is provided with a single wedge element used to sequentially drive staples similar to the manner shown in FIGS. 8A-9E below.

In the example pictured in FIGS. 7A-7C, two staples 30a are driven at the same time, but any number of staples could be driven similarly. Multiple drivers 52 and corresponding rows of staples can exist in the same tool. Once the driver 52 has fully driven the staples from the housing, it is returned to the home position. The return could be active, with operator input, as in the case of a separate hydraulic circuit, or cable to return the mechanism, or passive, with the driver returning on its own with forces supplied by a spring or springs which were compressed during actuation. In the illustrated embodiment, springs 55 compressed by the pushers 53 during staple firing return the pushers 53 to their original position in the housing after the driver has moved out of their path. A feed mechanism within the housing 12 advances another round of staples into the ready position for the next actuation as disclosed elsewhere in this application.

Figure 8A:
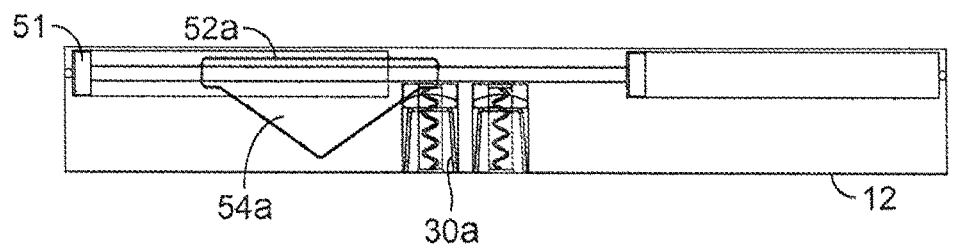
FIGS. 8A-8E are a sequence of side elevation views schematically illustrating movement of a second alternative staple driver to drive staples from a staple housing into tissue.
Figure 8B:
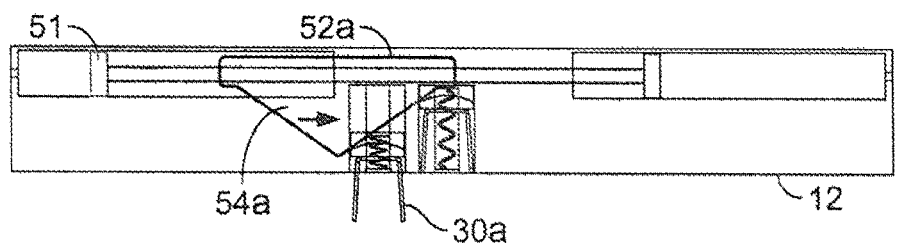
Figure 8C:
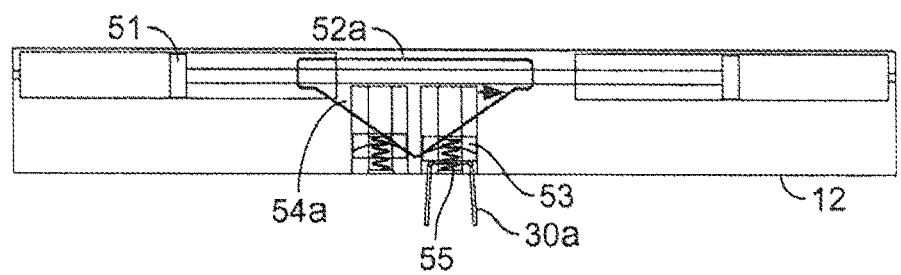
Figure 8D:
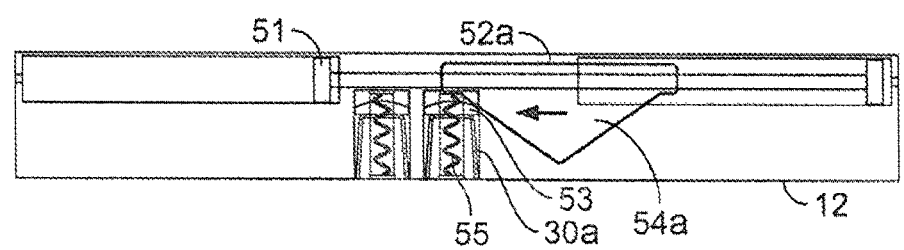
Figure 8E:
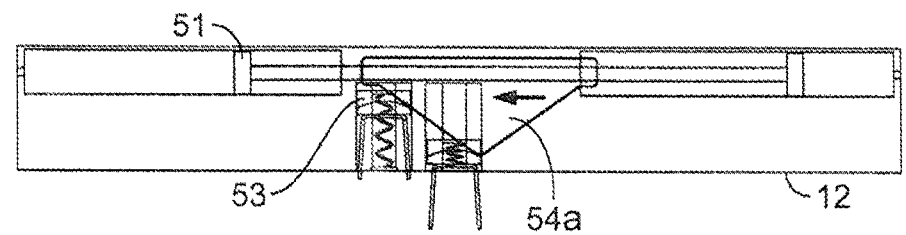

Another embodiment illustrated in FIGS. 8A-8E is similar to the FIG. 7A-7C embodiment, but it employs a bi-directional staple deployment scheme. As shown, driver 52a includes a wedge element 54a having two sloped edges. During movement of the driver 52a in a first direction, a first set of staples 30a, is sequentially driven into the tissue (FIGS. 8B and 8C). Once the first set of staples has been fired, another staple set can be brought into the ready positions (in the return path of the driver), such that the return motion of the wedge element 54a can deploy the second set into the tissue. In a modification to the FIG. 8A embodiment, a plurality of bi-directional wedge elements are positioned similar to the positions of the wedge elements in the FIG. 7A embodiment, allowing for simultaneous advancement using the multiple wedge elements on the driver. In this variation, movement of the driver in a first direction will drive a first set of staples and then movement of the driver in the opposite direction will drive the second set of staples fed into the ready positions vacated by the first staples.

Figure 9A:
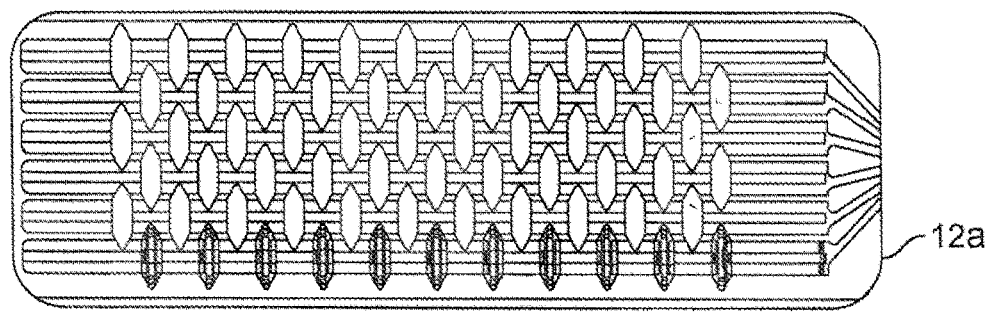
FIG. 9A shows a plan view of an alternate staple housing with the back plate removed.

In modifications to the embodiments of FIGS. 7A and 8A, the staples may be oriented in the staple housing such that the staple back spans are rotated 90 degrees from the position shown in FIGS. 7A and 8A (i.e. the staples are turned such that the back span extends into and out of the page in FIGS. 7A and 8A). One configuration using this design is shown in FIGS. 9A-9E. FIG. 9A shows the housing 12a with the back plate removed and shows only one row of drivers and staples for simplicity. In practice, each row would be filled with staples and each row could be driven into the anvil separately, or in groups, depending on the desired actuation scheme. Additionally, the staples could be arranged with the back spans at angles other than 90 degrees to the driver.

Figure 9B:
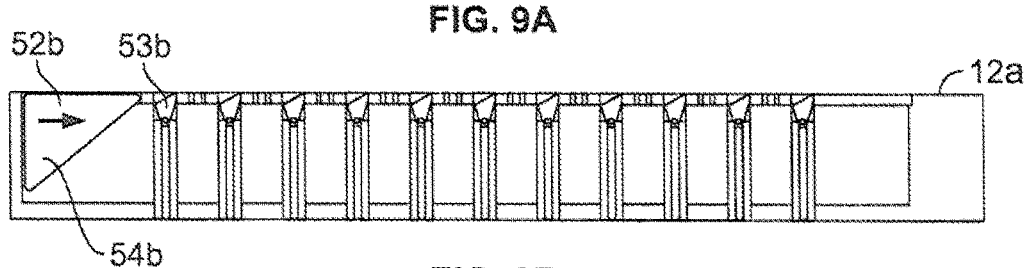
FIGS. 9B-9E are a sequence of side elevation views schematically illustrating movement of a staple driver to drive staples from the staple housing of FIG. 9A into tissue.
Figure 9C:
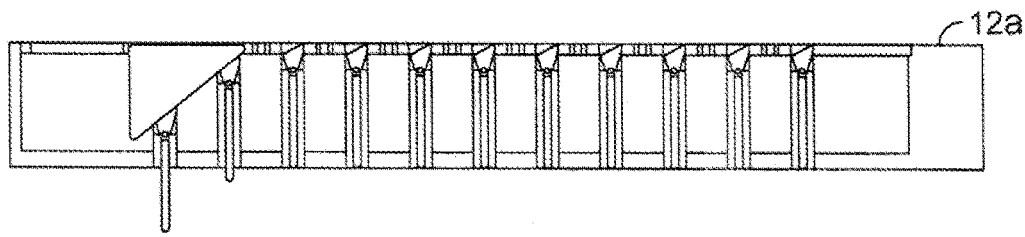
Figure 9D:
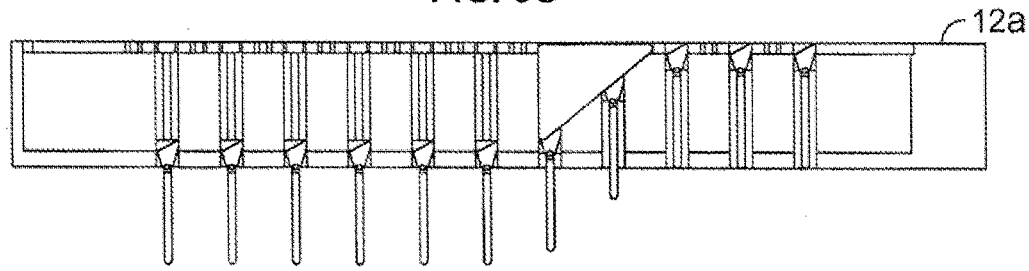
Figure 9E:
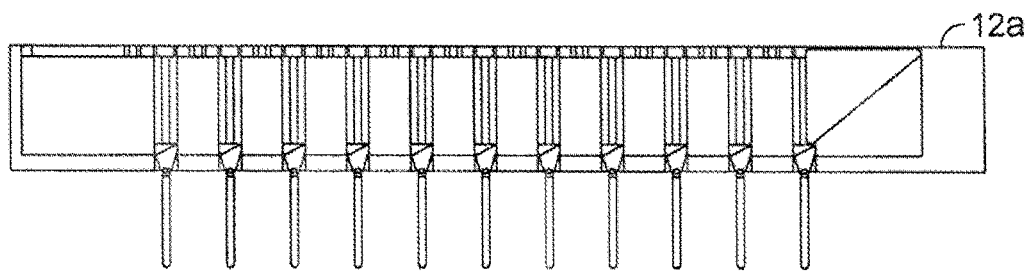

Referring to FIGS. 9B-9E, driver 52b includes a wedge 54b. The staple back spans are transverse to the direction of motion of the driver 52b. In FIG. 9B, the wedge is at its start position. To drive the staples, driver is pulled to the right by a cable, or other flexible element actuated by any means providing appropriate force. As the driver 52b travels, it forces the sloped caps 53b positioned above each the staple in a downward direction. The caps 53b drive the staples through the tissue and towards the anvil (not shown). As with the previous embodiments, a spring or other element may be used to return the caps to the original position.

Figure 10A:
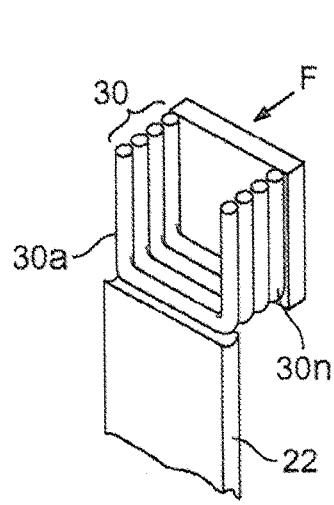
FIGS. 10A through 10C are a sequence of perspective views schematically showing driving of a staple from a ready position towards tissue to be stapled, and subsequent reloading of the next staple from the stack into the ready position.
Figure 10B:
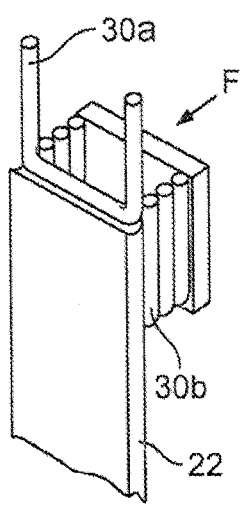
Figure 10C:
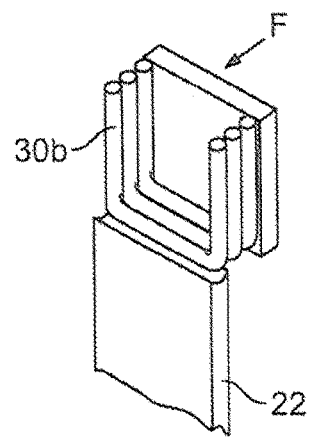

FIGS. 10A through 10C schematically illustrate operation of the staple pusher and automatic feed mechanism to fire a staple from the ready position and to then replace the fired staple in the ready position with the next staple in the stack. Referring to FIG. 10A, prior to staple firing, staple 30a is biased in the ready position due to the action of the spring force F imparted against the plate 34 by the spring (not shown in FIG. 10A). Staple pusher 22 is advanced as discussed above to fire the staple. FIG. 10B. Due to the constant spring force F against the plate 34, as soon as the staple 30a leaves the ready position, it is replaced in the ready position by the next staple 30b in the stack 30. FIG. 10C. This automatic reloading of staples into the ready position repeats itself as each staple 30a-30n in the cell is fired. After all staples 30a-30n have been fired, the staple housing may be reloaded with a new charge of staples if additional stapling is needed.

Figure 11:
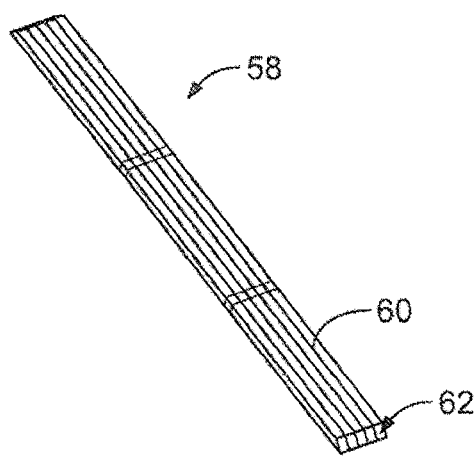
FIGS. 11 and 12 are perspective views illustrating one method of forming a staple stack for use in the stapler of FIG. 1A.
Figure 12:
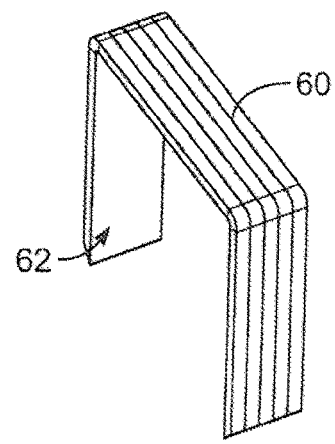

The stapler housings and staple cartridges disclosed herein may be used with any suitable staples or staple stacks. Staple stacks may be formed using a sheet of flat material 58 as shown in FIG. 11. Longitudinal score lines 60 are formed on one side of the sheet 58, and the ends 62 of the sheet are chamfered to create what will be the tips of the staple legs. The sheet 58 is bent into the shape shown in FIG. 12, with the score lines 60 serving as the dividing lines between what will become individual staples. With this arrangement, each time the staple pusher is driven, it causes the endmost staple to be sheared from the sheet of flat material and driven into the tissue.

Figure 13:
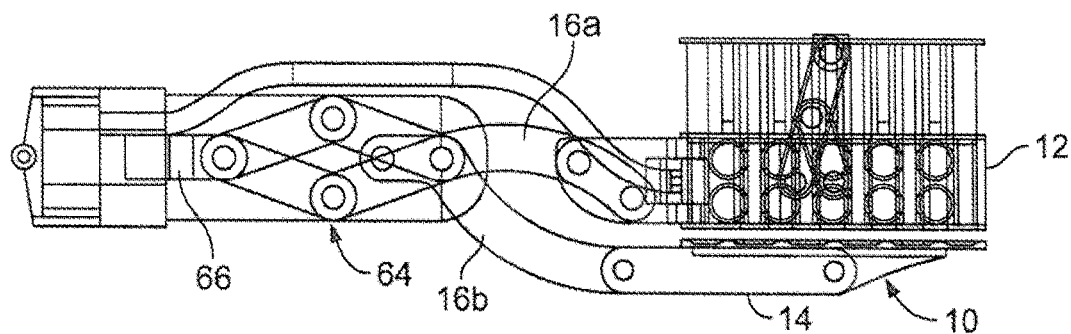
Figure 14:
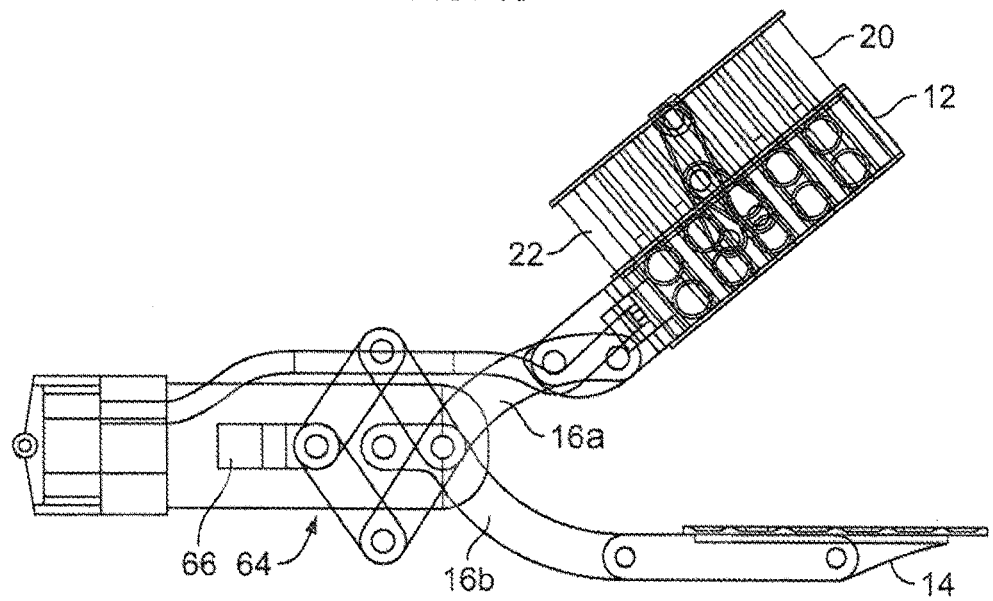

Use of the stapler 10 will next be described. Prior to use, staple stacks 30 are loaded into the cells of the staple housing 12. With the jaws 16a, 16b in the closed position as in FIG. 13, the staple head 10 is advanced to the location of the tissue to be stapled. Next, a control element on the handle of the stapler shaft is manipulated to open the jaws to the position shown in FIG. 14. Various configurations known to those skilled in the art may be used to open and close the jaws. The illustrated embodiment employs a linkage 64 coupled to the jaws 16a, 16b. Linkage 64 is actuated using a piston 66, which is moved distally using hydraulic or mechanical means to expand the linkage for opening the jaws (FIG. 14) and which is moved proximally to collapse the linkage and close the jaws (FIG. 13).

With the jaws 16a, 16b opened, the tissue to be stapled is positioned between the staple housing 12 and anvil 14. The stapler may be equipped with integrated tissue acquisition devices useful for this purpose. Suitable tissue acquisition devices are described in the following commonly owned applications: application Ser. No. 12/119,329, filed May 12, 2008, entitled DEVICES AND METHODS FOR STOMACH PARTITIONING, and application Ser. No. 12/050,169, filed Mar. 18, 2008, entitled ENDOSCOPIC STAPLING DEVICES AND METHODS, and application Ser. No. 12/268,216, entitled TISSUE ACQUISITION DEVICES AND METHODS, filed on same date herewith. In that application, tissue is acquired into a vacuum head using a vacuum source, and then the acquired tissue is retained (e.g. for tissue positioning, manipulation) by a grasper. Alternatively, separate instruments may be used to position tissue between the cartridge and anvil.

When an area of the stomach wall is drawn inwardly (bringing a two-layer "pinch" or fold of tissue toward the stomach exterior), corresponding regions of serosal tissue on the exterior of the stomach are positioned facing one another. According to a preferred method disclosed herein, two or more such areas or pinches of the stomach wall are engaged/grasped and drawn inwardly using instruments passed into the stomach via the mouth. The two or more pinches of tissue are held in complete or partial alignment with one another as staples or other fasteners are driven through the pinches, thus forming a four-layer plication. Over time, adhesions formed between the opposed serosal layers create strong bonds that can facilitate retention of the plication over extended durations, despite the forces imparted on them by stomach movement. A cut or cut-out may be formed in the plication during or separate from the stapling step to promote edge-to-edge healing effects that will enhance tissue knitting/adhesion and will ultimately contribute to the durability of the plication, despite the fact that mucosal tissue of one tissue pinch is positioned in apposition with the mucosal tissue of the other tissue pinch.

One or more such plications may be formed for a variety of purposes. For example, plications may be used to induce weight loss by creating a barrier or narrowing within the stomach that will restrict the flow of food from the proximal stomach towards the distal stomach. For example, a partition or barrier may be oriented to extend across the stomach, leaving only a narrow exit orifice through which food can flow from the proximal stomach to the distal stomach, or a similar antral barrier may be formed that will slow stomach emptying of stomach contents into the pylorus. In other cases, partitions or plications may be used to form a proximal pouch in the stomach or to reduce stomach volume to cause sensations of fullness after a patient eats relatively small quantities.

Coupled to or provided with the stapler are one or more, preferably two, three or more, tissue acquisition devices, which will also be referred to as "engagers" or "graspers" which are designed to engage tissue and draw the tissue into position between the stapler anvil and cartridge. In embodiments, the graspers are positioned to pass from one side of the "window" bounded by the stapler arms, through the window, and used to grasp tissue on the opposite side of the window. These graspers are then withdrawn back through the window to draw the grasped tissue between the cartridge and anvil. In other embodiments, the arms can engage tissue and draw it between the cartridge and anvil without necessarily passing through the window. Such embodiments include the arms oriented angularly relative to one another when viewed along the longitudinal axis of the device shaft.

The graspers can be simple alligator or forceps type graspers, vacuum chambers, corkscrews which can be traditional corkscrews or gear-driven perpendicular corkscrews, hooks, or any combination thereof, such as a corkscrew in combination with a vacuum chamber.

The term "grasper" is used to refer generally to any type of tool that can be used to engage or acquire tissue via any means (grasping, hooking, penetration, suction, adhesion, etc.) so the acquired tissue can be positioned between the staple holder and anvil. Similarly, even though some of the disclosed graspers do not physically "pinch" tissue, the term "pinch of tissue" may be used in this disclosure to refer to a fold, area, or tab of tissue acquired using a grasper for positioning of the that fold, area, or tab between the staple holder and the anvil.

Plugs/pledgets within the cut holes may be used to hold two or more two-layer plications together. For example, rather than joining two pinches of tissue as disclosed above to form a four-layer plication, the stapler may be used to separately staple and cut each pinch, forming a plurality of two-layer plications. Afterwards, pairs (or larger groups) of the two-layer plications may be joined together to position the cut holes into alignment, and the plugs/pledgets may be inserted through the aligned holes to retain the plications. Plugs/pledgets passed through the hole in one or more two- or four-layer plication can function as restrictive devices themselves, and may be used to restrict flow of food towards the distal stomach.

Figure 15:
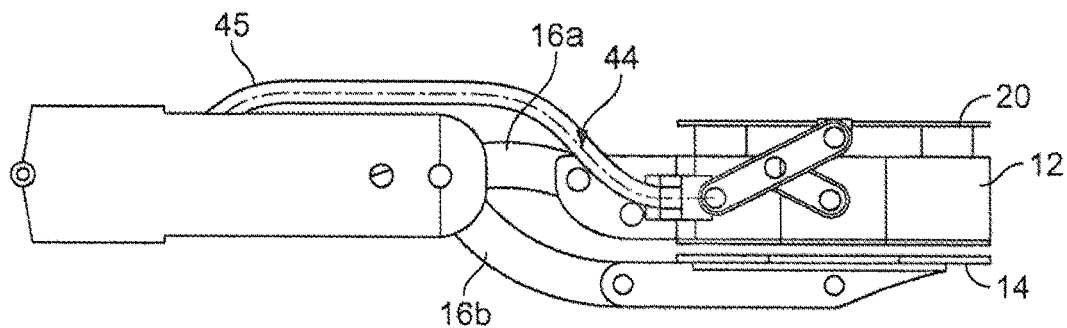

Once tissue is between the cartridge and anvil, the jaws are again closed (FIG. 13) to close the staple housing and anvil against the tissue, thereby compressing the tissue in preparation for stapling. The cable 44 (FIG. 1A) is actuated to drive the staple driver 20 towards the staple housing 12, thus driving the staple pushers 22 into the staple housing 12 (FIG. 15) to fire the array of staples through the tissue. As is typical with staplers, the free legs of the staples fold against corresponding recesses (not shown) on the anvil surface.

When tension is released from the cable 44, springs (not shown) force the staple driver 20 back into the retracted position shown in FIG. 13. Once the staple driver 20 withdraws from the staple housing, a new staple moves into the ready position in each cell (as described in connection with FIGS. 10A through 10C), immediately readying the stapler for deployment of a second staple array.

Figure 16:
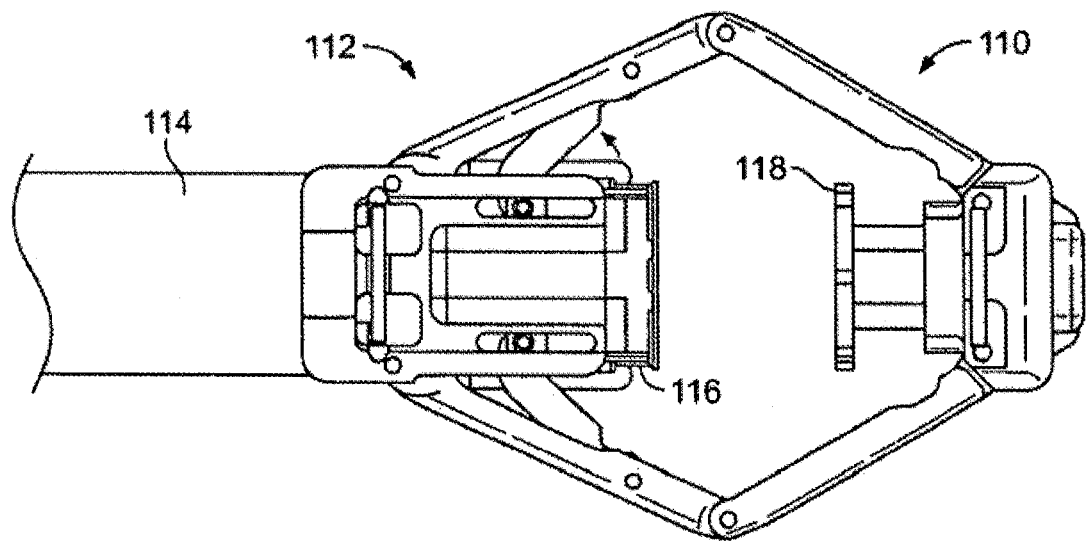
FIG. 16 is a plan view of a second embodiment of a stapler employing an alternate multi-fire staple housing.

FIG. 16 is a side view of an alternate embodiment of a multi-fire stapler 110. Stapler 110 includes a stapler head 112 mounted to an elongate shaft 114. A staple housing, which may be a replaceable staple cartridge 116, and an anvil 118 are positioned on the stapler head 112. The stapler head 112 is equipped with linkages operable to decrease the distance between the cartridge and anvil for tissue compression and stapling. These features, as well as others (e.g. hydraulic and piston arrangement, cutting features, etc.) suitable for inclusion in the stapler 110, are disclosed in commonly owned application Ser. No. 12/050,169, filed Mar. 18, 2008, entitled ENDOSCOPIC STAPLING DEVICES AND METHODS, which is incorporated herein by reference.

Like the staple housing of the first embodiment, cartridge 116 is a multi-fire unit configured to simultaneously fire an array of staples, and to automatically reload a subsequent array of staples ones the first array has been discharged. The staples in the array can be arranged in a variety of patterns, including but not limited to the square pattern shown in connection with the FIG. 16 embodiment.

In embodiments, tissue is drawn inwardly into a vacuum chamber, although tissue may be drawn inwardly using other components (e.g. graspers) that do not involve the use of a vacuum. When a portion of the interior stomach wall is drawn inwardly, sections of serosal tissue on the exterior of the stomach are positioned facing one another. The disclosed fastener applying device allows the opposed section of tissue to be moved into contact with one another, and delivers fasteners that will hold the tissue sections together until at least such time as serosal bonds form between them.

The system may include a stapler having a stapler head positioned on a distal portion of a shaft. A handle on the shaft controls articulation of the stapler head and actuation of the tissue acquisition, tissue compression, and stapling functions of the stapler head. Vacuum and fluid sources are fluidly coupled to the handle for use in tissue acquisition, compression and stapling as discussed below. The vacuum source may be the "house vacuum" accessible through a coupling on the wall of the operating room, or an auxiliary suction pump. The stapler may include a switch allowing the user to control airflow between the vacuum source and stapler.

Figure 17:
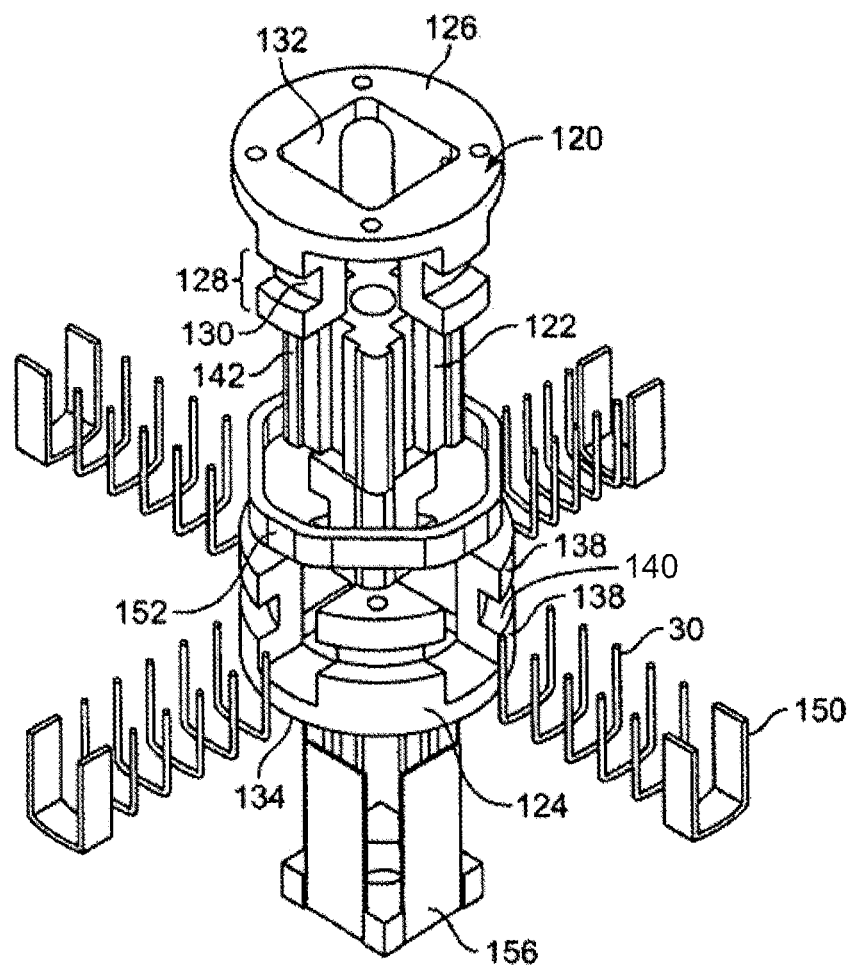
FIG. 17 is an exploded view of the staple cartridge of the FIG. 16 stapler.
Figure 18:
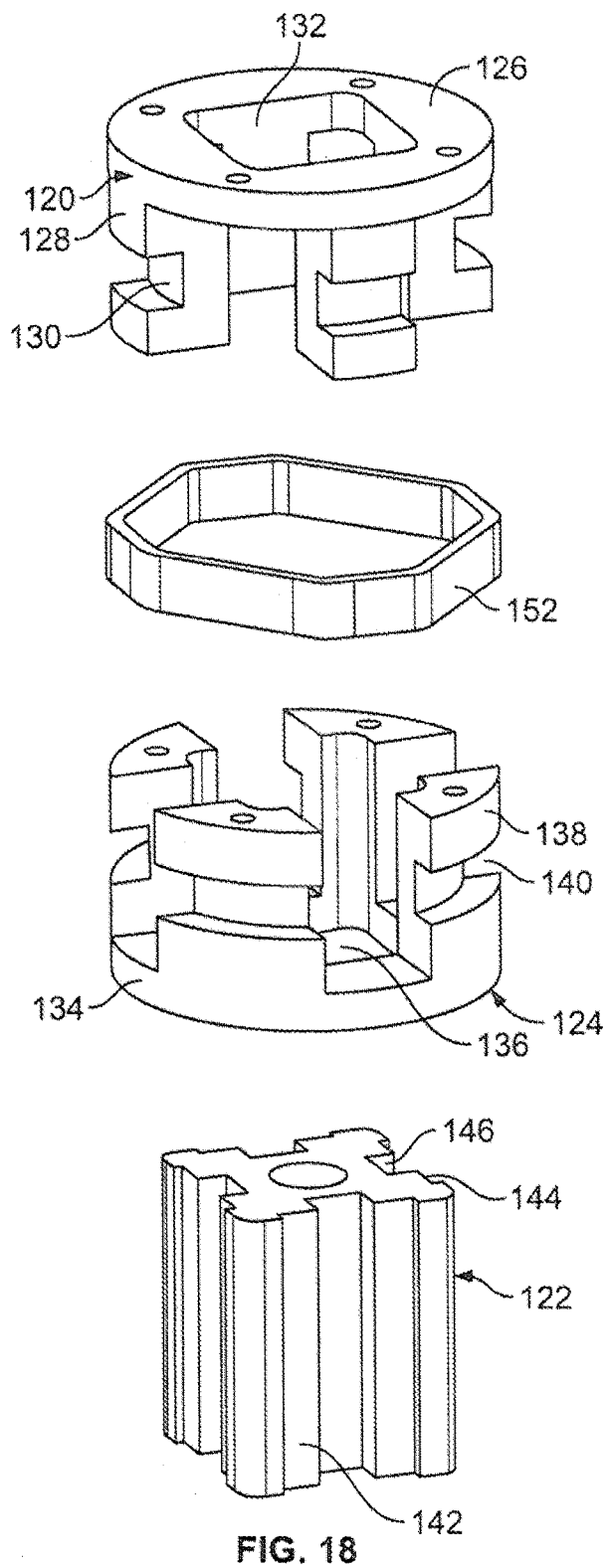
FIG. 18 is another exploded view of the staple cartridge of FIG. 17, in which the staples, staple advancing elements, and staple pusher are not shown for clarity.

Features of the cartridge 116 will first be described with reference to the exploded views shown in FIGS. 17 and 18. The cartridge includes a front housing 120, middle housing 122 and a rear housing 124. The front housing 120 is positioned at the distal end of the cartridge and includes a plate 126 that contacts the tissue to be stapled during stapling. Spaced apart members 128 extend longitudinally from the plate 126 in a proximal direction. Each of the members 128 includes a circumferential channel 130. The plate 126 includes a central cutout 132 proportioned to receive middle housing 122.

Rear housing 124 has a plate 134 with a cutout 136 proportioned to receive the middle housing 122. Spaced apart members 138 extend longitudinally from the plate 134 in a distal direction. Members 138 have circumferential channels 140.

Middle housing 122 includes longitudinal sidewalls 142 proportioned to allow the middle housing 122 to slide into the central cutouts 132, 136 of the front and rear housings. Each of the sidewalls 142 has a longitudinally extending first channel 144 centrally positioned on the sidewall 142, and a longitudinally extending second channel 146 centrally positioned within the first channel 144.

Figure 21A:
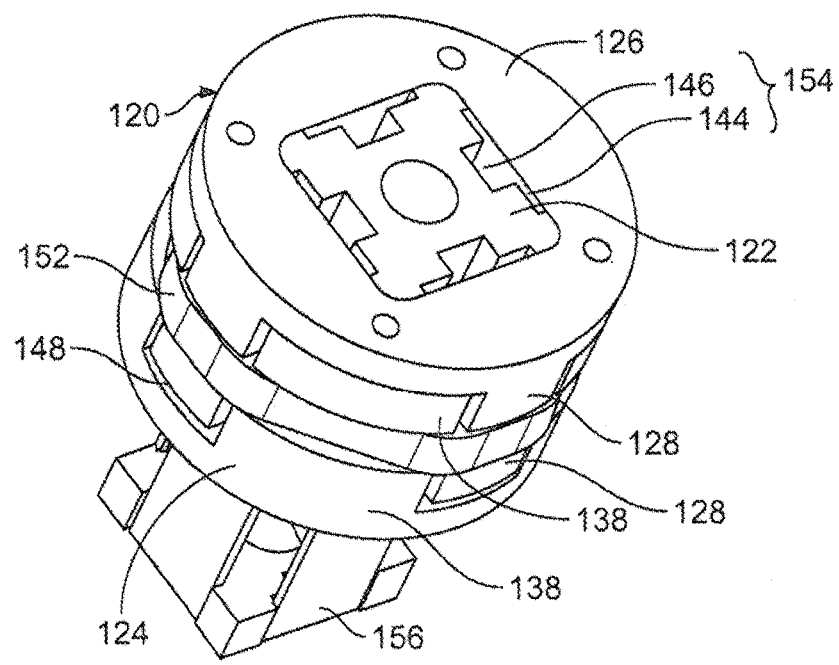
FIG. 21A is a perspective view of the staple cartridge of FIG. 17, with the staple pusher in the retracted position.

As shown in FIG. 21A, in the assembled cartridge, the middle housing 122 extends between the cutouts of the front and rear housings. The longitudinally extending members 128 of the front housing 120 are disposed between the longitudinally extending members 138 of the rear housing such that the channels 130 of the walls 128 are aligned with the channels 140 of the walls 138, forming a continuous circumferential channel extending around the cartridge 116. As discussed in greater detail below, a compression band 152 (also see FIG. 18) is positioned in this circumferential channel.

Figure 21B:
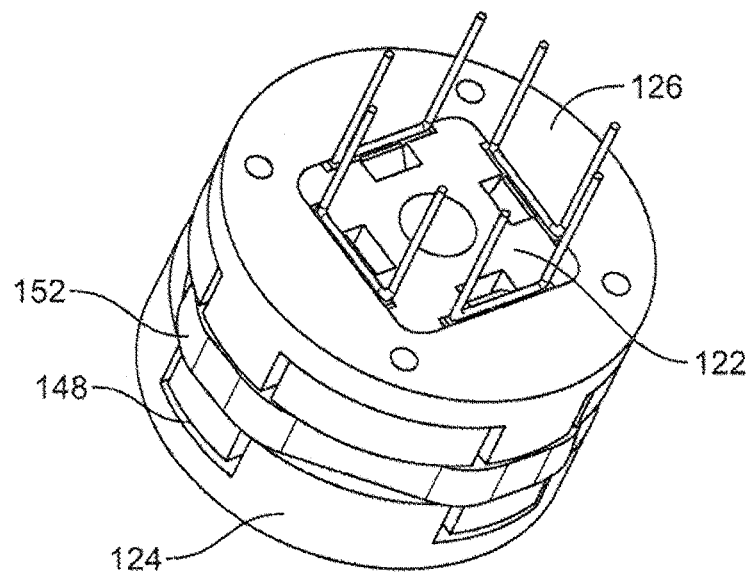
FIG. 21B is similar to FIG. 21A and shows the staple pusher in the staple driving position to drive staples from the staple cartridge.
Figure 22:
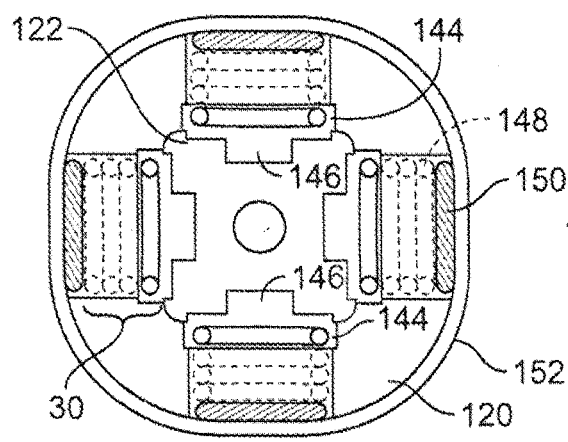
FIG. 22 is a top plan view of the staple cartridge of FIG. 17, showing in hidden lines the staple stacks and staple advancing elements.

When housings 120, 122, 124 are assembled, spaces between their various walls form chambers within which staples are positioned during use. Referring to FIGS. 21A and 21B, rectangular U-shaped chambers 148 are disposed between each of the longitudinally extending members 128 and its neighboring members 138. FIGS. 17 and 22 illustrate that a stack or collection of staples 30 is disposed in each of the chambers. A total of four such chambers 148 are shown, corresponding to four stacks of staples for the illustrated embodiment.

Each staple is positioned in its corresponding chamber with its legs disposed in the longitudinally extending branch of the chamber, and with the cross-member or back span of the staple in the laterally extending portion of the chamber. Each of the chambers 148 also houses rectangular U-shaped staple advancing element 150 adjacent to the radially outermost one of the staples 30.

Compression band 152 is disposed within the circumferential channel formed by the aligned channels 130, 140. The inner wall of the compression band is in contact with the longitudinally extending legs of each of staple advancing elements 150 in the cartridge. The radially inward spring forces of the compression band bias the staple advancing elements 150, and thus all of the staples, in radially inward directions.

Referring again to FIG. 22, the longitudinal channels 144, 146 of the middle housing 122 form a chamber 154 with the walls bordering the cutouts in the front and rear housings 120, 124. The innermost staple 30a in each stack is biased into the chamber 154 by the radially inward forces of the compression band 152. A staple in the chamber 154 is in the ready position, ready for advancement from the cartridge into adjacent tissue.

Figure 19:
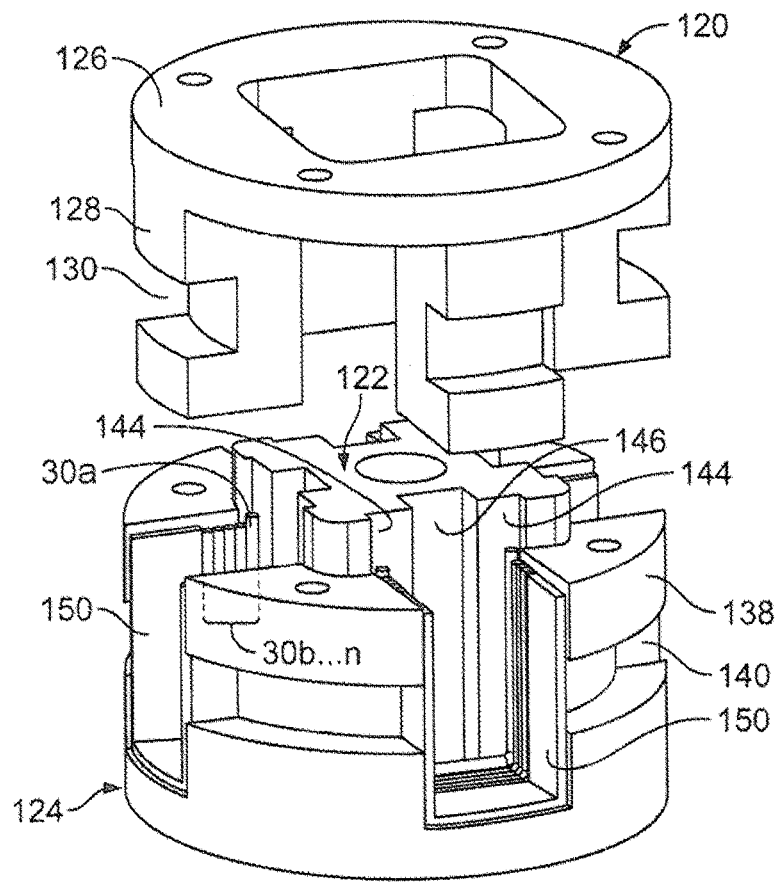
FIG. 19 is a perspective view of the staple cartridge of FIG. 17 in a partially assembled state, with staples and staple advancing elements loaded, but with the front housing separated to permit viewing of the staples and staple advancing elements. The compression band and staple pusher are not shown.

FIG. 19 shows the front and rear housings aligned for insertion of the elements 128 of the front housing between the elements 138 of the rear housing. This figure best shows the positions of the ready position staple 30a, the remaining staples 30b-n, and the staple advancing element 150 for a given stack. As shown, the ready position staple 30a is biased against the wall of the middle housing 122 lining the first channel 144. The compression band 152 is removed for clarity.

Figure 20:
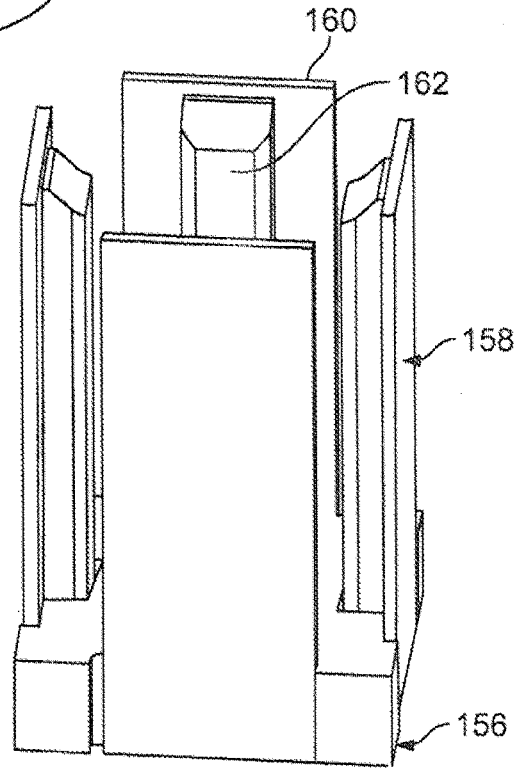
FIG. 20 is a perspective view of the staple pusher for the staple cartridge of FIG. 17.

A staple pusher assembly 156 (FIGS. 17 and 20) is provided for driving staples that are in the ready position from the cartridge into the tissue. Staple pusher assembly 156 includes pusher elements 158 slidable in a distal direction within corresponding ones of the chambers 154. Each pusher element has a plate 160 that slides through a corresponding one of the channels 144 of the middle housing (FIG. 19), to drive the ready position staple 30a biased into that channel. A rib 162 on the inwardly facing surface of the plate 160 slides through the associated channel 146 to maintain proper alignment of the pusher assembly 156 with the middle housing. Pusher assembly 156 may be advanceable by means of a hydraulically activated piston as described in commonly owned application Ser. No. 12/050,169, filed Mar. 18, 2008, entitled ENDOSCOPIC STAPLING DEVICES AND METHODS, or by other means.

Figure 23A:
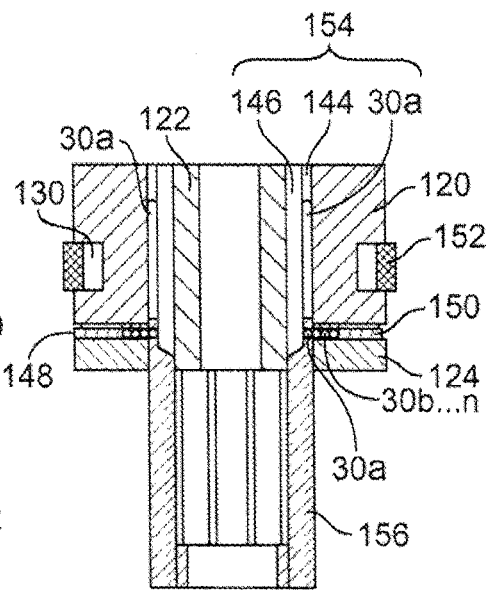
FIGS. 23A through 23C are a sequence of cross-section views of the cartridge showing driving of staples from a ready position towards tissue to be stapled, and subsequent reloading of the next staples from the staple stacks into the ready position.
Figure 23B:
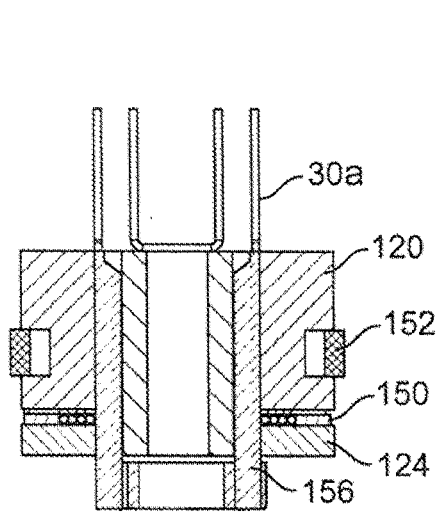
Figure 23C:
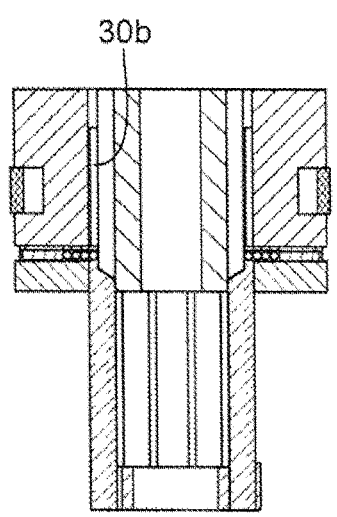

FIGS. 23A through 23C are a sequence of cross-section views illustrating staple firing and subsequent reloading of the staple positions in preparation for an additional firing. FIG. 23A shows the cartridge prior to the firing of the first array of staples. As shown, the pusher assembly 156 is in the fully retracted position. The most radially inwardly positioned staples 30a of each staple stack 30 are disposed in the ready position in chamber 154. The second, third etc. staples 30b-n of each stack are positioned in the chamber 148. In the FIG. 23A view, only the cross-pieces of the staples 30b-n are visible (in transverse cross-section) along with the corresponding portion of the U-shaped chamber 148. FIG. 23B shows the position of the pusher assembly 156 as it completes the process of pushing staples 30a from the cartridge. The anvil, against which the legs of each staple fold, is not shown in FIGS. 23A-C.

The pusher assembly is next retracted as shown in FIG. 23C The radially inward forces of the compression band 152 against the staple advancing element 150 push the next staple in each stack into the ready position (i.e. in channel 144) vacated by the first staples to be driven. The stapler head may be repositioned to a second tissue area to be stapled, at which time the pusher assembly is again advanced to drive the second array of staples into the tissue. The process is repeated until the desired number of arrays has been applied to tissue, and/or until the staple sets have been exhausted. If additional staples are needed after the cartridge has been emptied of all staples, the stapler head is withdrawn from the patient, and the cartridge may be removed from the stapler and replaced with one filled with staples. Alternatively, the existing cartridge may be refilled by removing the compression band and the staple advancing elements, inserting staples in the chamber 154, and then replacing the staple advancing element and the compression band.

The disclose multi-fire staple housings are useful in carrying out a number of procedures, including but not limited to stomach partitioning and/or the formation of stomach wall plications for use in retaining implants.

For example, the disclosed multi-fire housings may be employed in a stomach wall partitioning system. When an area of the stomach wall is drawn inwardly (bringing a two-layer "pinch" or fold of tissue toward the stomach exterior), corresponding regions of serosal tissue on the exterior of the stomach are positioned facing one another. In stomach wall partitioning methods disclosed in commonly owned application Ser. No. 12/119,329, filed May 12, 2008, entitled DEVICES AND METHODS FOR STOMACH PARTITIONING, two or more such areas or pinches of the stomach wall are engaged/grasped and drawn inwardly using instruments passed into the stomach via the mouth. The two or more pinches of tissue are held in complete or partial alignment with one another as staples or other fasteners are driven through the pinches, thus forming a four-layer tissue plication.

Multiple plications of this type may be used to induce weight loss by creating a barrier or narrowing within the stomach that will restrict the flow of food from the proximal stomach towards the distal stomach and/or that will effectively reduce stomach volume to cause sensations of fullness after a patient eats relatively small quantities. A partition formed using plications might also be used as a treatment for GERD to create a shield between the stomach and esophagus that will minimize reflux.

Commonly owned application Ser. No. 12/175,242, filed Jul. 17, 2008, entitled ENDOSCOPIC IMPLANT SYSTEM AND METHOD and application Ser. No. 12/050,169, filed Mar. 18, 2008, entitled ENDOSCOPIC STAPLING DEVICES AND METHODS describe formation of plications by drawing a pinch of stomach wall tissue inwardly to form a tissue fold, and by then applying staple arrays or other fastening means to the tissue fold to retain the plication. Holes may be formed in the plications for receiving implants or anchors to which additional implants will be coupled.

The disclosed multi-fire staple housing will greatly facilitate these types of procedures by allowing serial formation of each of the required plications without necessitating removal of the stapler head from the stomach after formation of each plication. In other words, after a staple array is applied, to tissue to create a plication, the staple head may be immediately repositioned and used to create second and subsequent plications, all without the need to remove the stapler head from the body for reloading or replacement with a fresh stapler. Thus, a stomach wall partition or a collection of plications may be formed in less time than was previously possible.

In addition to the staple arrangements disclosed above, alternative arrangements are suitable and can be used with feed mechanisms of the type disclosed above.

In one alternate staple arrangement, staples are formed into chains such that the legs are adjacent and the back spans do not touch. The arrangement would look like this: UUUUUUUU, although overlap of the staple elements is also possible. As one staple in the chain is driven from a ready position in the staple housing, and the driving member retracted, the next staple is moved into the ready position, with the feed motion primarily along the axis of the back span of the staple. Staples may be fired singly, or in multiples at the same time or at alternating times with one group (or single staple) firing while another group (or single staple) is reloading.

In a radial or "revolver" type staple arrangement, staples are arranged like spokes of a wheel, housed within, a wheel, or on a belt, with the staple legs, and direction of driving generally parallel to the axis of the wheel (like the bullets in the chamber of a revolver). As an example, 3 of the 12 staples (either equally spaced about the ring or not) could be advanced, then the driving member is retracted and either the driving member indexed to the next three staples, or the staple magazine is indexed such that the next three staples are aligned with the driver. This motion could continue for 4 total firings of 3 staples each. In a modified, ferris wheel type arrangement, the staples are oriented with the staple legs perpendicular to the axis of the wheel, or in a non-circular belt. In this case, the driver would drive staples toward the outside from the inside, or toward the inside from the outside of the wheel or belt.

Other embodiments use flat nested arrangements of staples. For example, a low profile way of storing the staples would be to lay them flat on each other with each one slightly in front of the previous one, like dominoes after they have fallen. In this case, a method of tilting up the staple to be driven would be used. Double forming without tilting would also make this possible. In this instance, staples would be pushed forward and bent down, then crushed to the traditional B shape.

In another arrangement, the array or magazine of staples consists of a chain of groups of staples. The staples are housed in a link of the chain which is designed to interface with the driving member. When a link of the chain, with one to 5 or more staples is advanced to the driver, those staples may be driven. Upon retraction of the driver, the chain is advanced and the spent link is pushed beyond the driving zone and a new link is advanced into the driving zone. The spent links could move to a containment area, or proceed out of the device. Similarly, the loaded links could be housed in a containment area, or extend beyond the envelope of the device. If the material of the chain in this example, or any mentioned elsewhere in this description, were biocompatible, or bioabsorbable, the links of the chain could be discarded in the lumen or incorporated into the staple line such that no, or less, spent chain material required post-firing management.

Figure 24:
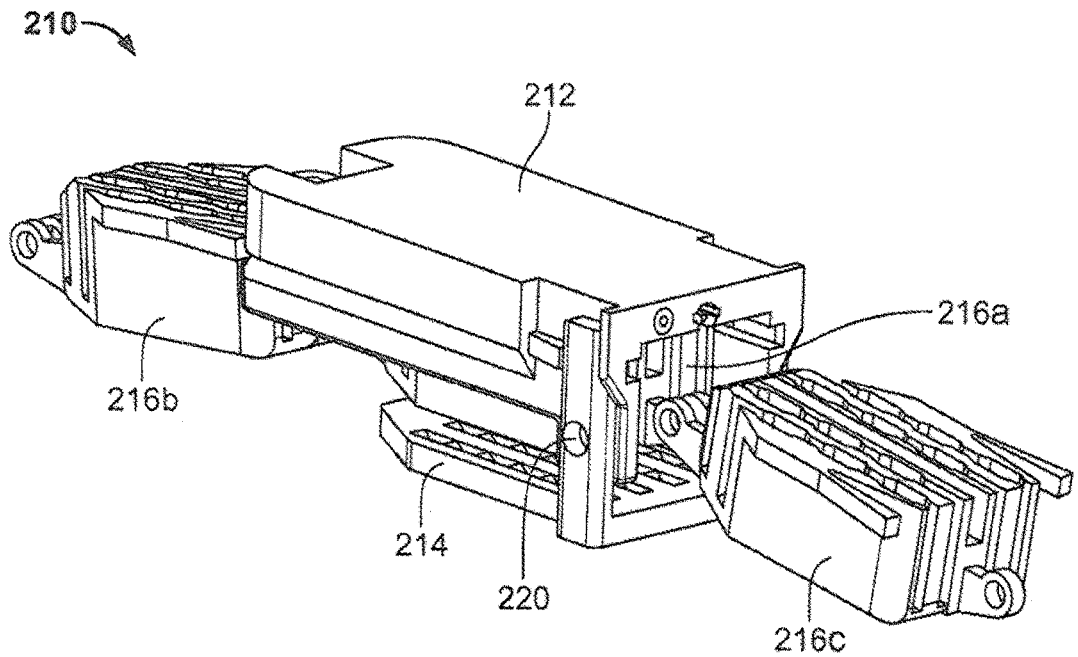
FIG. 24 is a perspective view of an alternative embodiment of a staple head, in which a spent cartridge is positioned in the background, a second cartridge is within the staple housing, and a third cartridge is awaiting advancement into the staple housing to replace the second cartridge.

One embodiment of a stapler employing this concept will next be described. FIG. 24 illustrates a stapler head 210 including a housing 212 and an anvil 214. Three staple cartridges 216a-c are shown. Cartridge 216a, shown coupled to the housing 212 and facing anvil 214, contains a plurality of staples and is position for staple delivery, i.e. to receive a driver that will fire the staples from the cartridge into tissue disposed between the cartridge and anvil. Cartridge 216b, which has already been fired, is in the background. Another cartridge 216b is in the foreground, waiting to be advanced into position between the cartridge and anvil for reloading of the stapler. The cartridges 216a-c are flexibly linked together.

Figure 25:
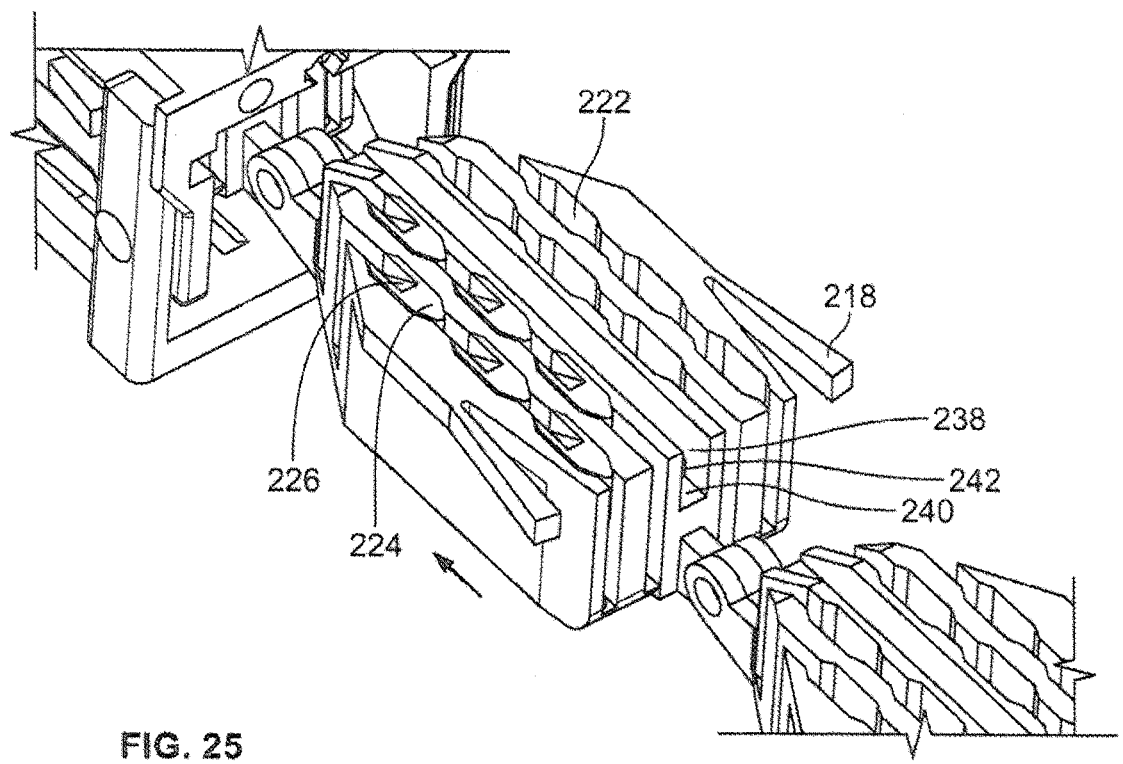
FIG. 25 is a perspective view illustrating a first cartridge advancing into the staple housing and a second cartridge coupled to the first cartridge.

FIG. 25 shows a close-up view of the cartridge 216a prior to its advancement into the housing 212. Wings 218 at the end of the cartridge will flex inward as the cartridge passes through the anvil extensions above the anvil pivot 220. Once they are past the anvil extensions, they spring outward and when stapling forces are applied to drive staples from the cartridge towards the anvil, the cartridge will slide backward slightly and the wings will push on the anvil extensions above the anvil pivot. This will help to keep the anvil aligned with the cartridge face, even as stapling forces push them apart.

As best shown in FIG. 25, each cartridge includes a plurality of slots 222 proportioned to receive a plurality of staples. Caps 224 are positioned above the back spans of staples in the slots. Caps 224 are shown in only two of the slots 222 in FIG. 25. Each cap 224 includes a sloped surface 226. During use, each of the four slots 222 may be filled with staples and caps 224.

Figure 26C:
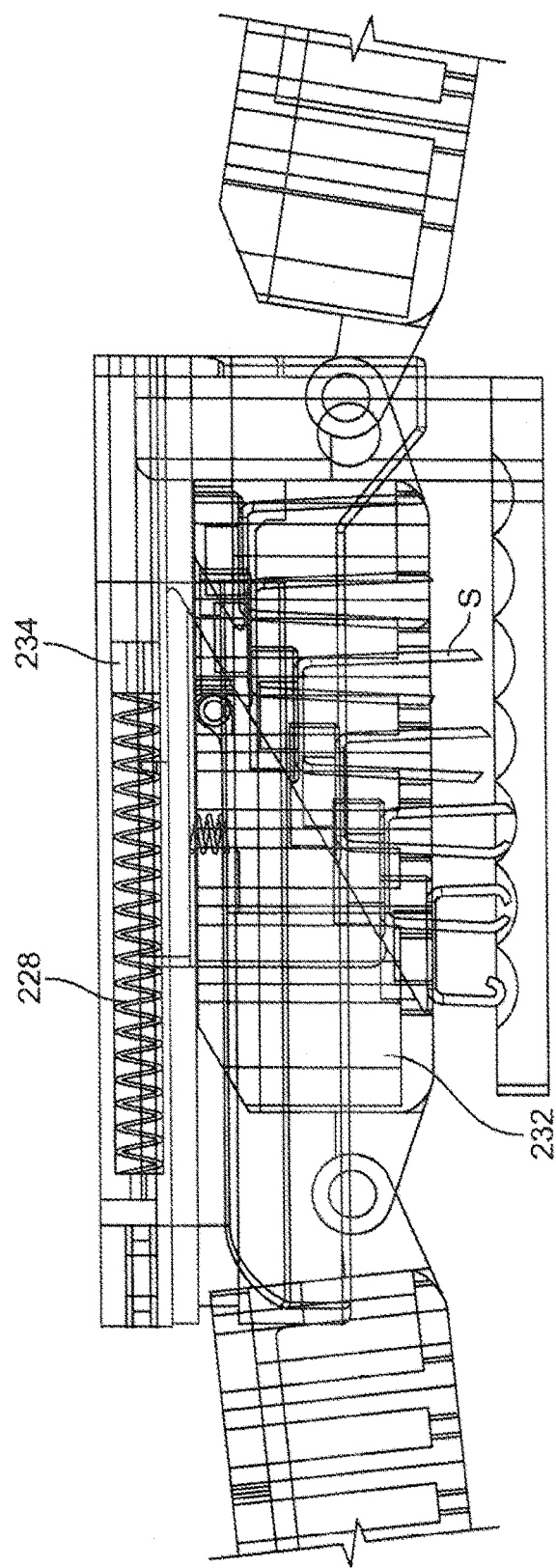

Referring to FIG. 26A, a driving wedge 232 has four wedge-shaped plates (only one of which is visible), each extending into one of the slots 222. A cable pull or other mechanism is provided for advancing the driving wedge longitudinally through the housing 210 (from left to right in the illustrated drawings) so that the wedge-shaped plates move through the slots 222. The wedge-shaped plates are positioned such that when they travel in the slots, they contact the caps 224 corresponding to the various staples S (FIGS. 26A-E) within a given slot 222 in a manner similar to that described in connection with FIGS. 9B-9E, thereby driving the staples into tissue positioned between the housing and anvil.

Spring 228 is disposed in a channel in the housing 212 and is configured such that it is compressed as the driving wedge 232 is moved by the user actuating a cable or other force transfer element. For example, the wedge 232 might be coupled to a cable extending through the spring 228 and attached to cap 234 on the spring 228 such that as the wedge moves to the right in FIG. 26A, the cable pulls the cap 234 to the left to compress the spring. A second spring 230 is attached to the driving wedge 232 and is compressed by a lever 236 riding in a groove 238 (FIG. 25) in the cartridge. This groove 238 increases in depth at the end of the wedge's stroke, thus providing a notch 240 for the lever 236 to fall into at the end of its travel.

Figure 26D:
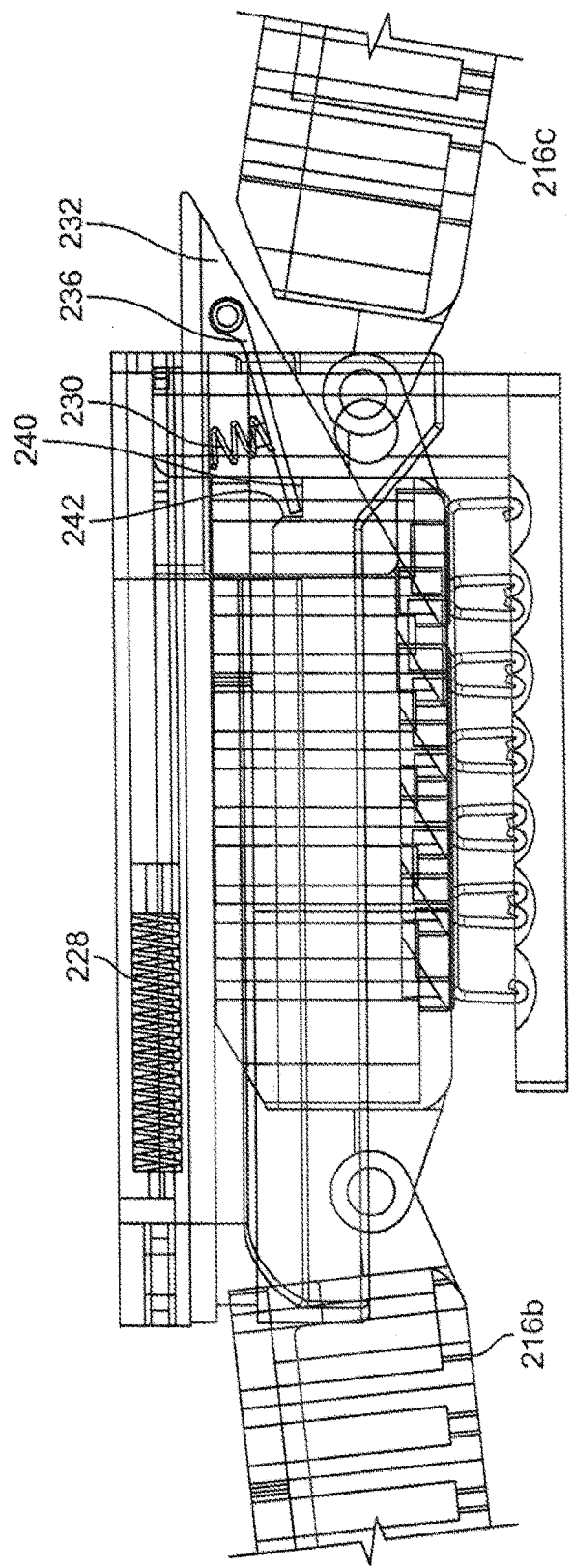
Figure 26E:
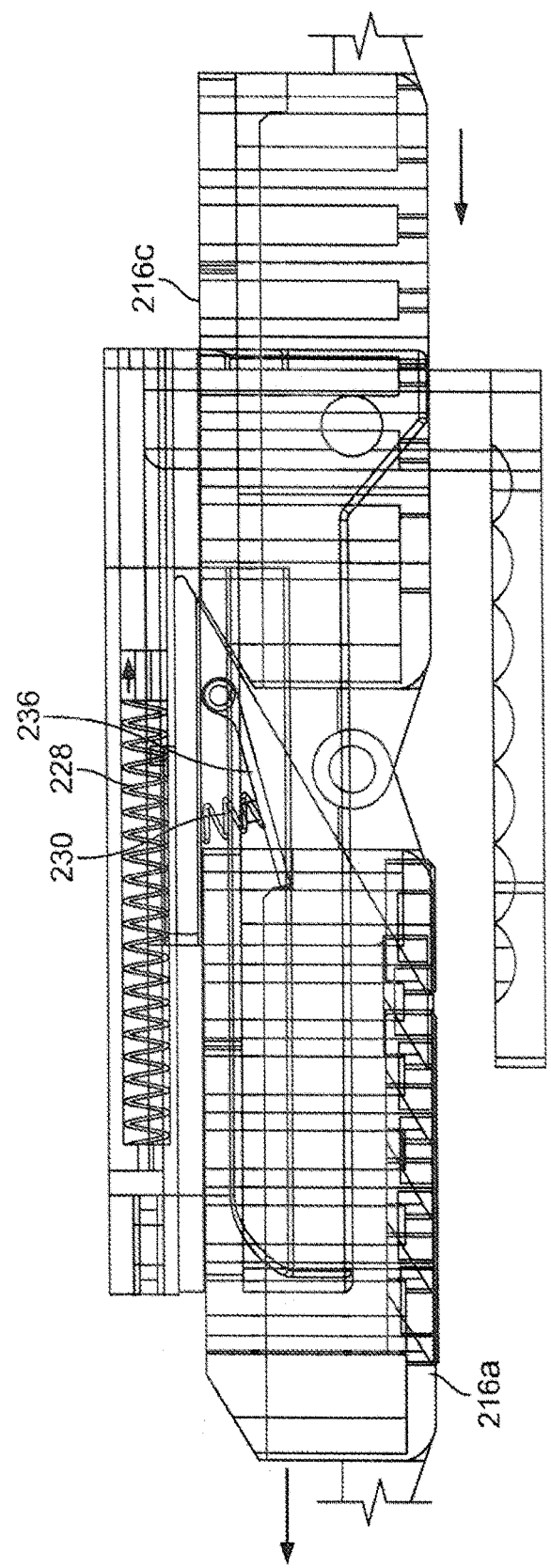

FIG. 26A shows the staple head 210 after staples have been fired from cartridge 216b and after cartridge 216a has been moved into the housing such that its staples are in staple delivery positions ready for firing. FIGS. 26A-26C show stages of staple deployment as the wedge 232 is drawn over the staple driving elements or caps 234. The wedge 232 moves from the home position (FIG. 26A) through the cartridge to deploy the staples through the tissue, such that their legs fold against the anvil 214. As the wedge advances, the spring 228 is compressed. As the wedge reaches the end of its travel, lever 236 pivots into the notch 240 as shown in FIG. 26D. When the user stops pulling on the wedge (e.g. by releasing a pull cable), the loaded return spring 228 will unload, driving the wedge 232 and lever 236 towards the home position, which is towards the left in the FIG. 26A-E drawings. The lever 236 pushes against wall 242 of the groove 238, thus driving the spent cartridge 216a out of the stapler (FIG. 26E) while drawing in the next loaded cartridge 216b that is coupled to the cartridge 216a.

The stapler is repositioned and the sequence is repeated until all the cartridges have been fired, or until stapling is complete.

It may be advantageous to maintain a level of mechanical simplicity comparable to currently produced linear staplers, but enable multi-fire capability without the need to withdraw the stapler from the patient. In this design, the spent cartridge is made to be ejected and be dropped in place, or be tethered or otherwise connected to the stapler or to the next cartridge to be loaded into the stapler. Loading would be accomplished with tools already in the patient, or with additional mechanisms within the tool itself, which would form or act as a conveyor of, or conduit for, new cartridges being advanced to the stapler head.

The above, groupings are not exclusive and, for example, radial driver or magazine motion could be combined with stacked, flat nested, or chained staple arrangements.

It should be recognized that a number of variations of the above-identified embodiments will be obvious to one of ordinary skill in the art in view of the foregoing description. Moreover, features of the disclosed embodiments may be combined with one another and with other features (including those taught in the prior applications referenced herein) in varying ways to produce additional embodiments. Accordingly, the invention is not to be limited by those specific embodiments and methods of the present invention shown and described herein. The applications and methods listed are not limited to the treatment of diseases or procedures listed. Modifications of the above described methods and tools and variations of this invention that are obvious to those of skill in the art are intended to be within the scope of this disclosure.

Any and all patents, patent applications and printed publications referred to above, including those relied upon for purposes of priority, are incorporated herein by reference.

We claim:

1. A method for stapling tissue, comprising:
   inserting a stapler into a body cavity of a patient, wherein the stapler includes an anvil and a staple member including a plurality of staples, the staple member and the anvil configured to relatively move towards and away from each other along an axis, wherein the plurality of staples are oriented radially with respect to the axis; and
   driving a first set of staples from the staple member towards the anvil, wherein the first set of staples (a) includes multiple staples equally spaced from the axis, and (b) includes less staples than the plurality of staples.

2. The method of claim 1, wherein the multiple staples of the first set of staples are symmetrically arranged about the axis.

3. The method of claim 1, wherein the plurality of staples are symmetrically arranged about the axis.

4. The method of claim 1, further comprising using a vacuum to draw tissue between the staple member and the anvil.

5. The method of claim 1, wherein the stapler includes a plurality of linkages coupling the staple member and the anvil.

6. The method of claim 1, further comprising moving a staple driver in a direction generally parallel to the axis to drive the first set of staples from the staple member.

7. The method of claim 1, further comprising driving a second set of staples of the plurality of staples from the staple member towards the anvil, wherein the second set of staples are (c) equally spaced from the axis, and (d) equal in number to the first set of staples.

8. The method of claim 7, further comprising rotating at least one of a staple driver or the staple member after driving the first set of staples to align the second set of staples with the staple driver.

9. The method of claim 7, further comprising driving a third set of staples of the plurality of staples from the staple member towards the anvil, wherein the third set of staples are (e) equally spaced from the axis, and (f) equal in number to the first set of staples.

10. A method for stapling tissue, comprising:
inserting a stapler into a body cavity of a patient, wherein the stapler includes an anvil and a staple member having a plurality of staples, wherein the staple member and the anvil are configured to relatively move towards and away form each other along an axis;
driving a first set of staples from the staple member towards the anvil;
after driving the first set of staples, rotating at least one of a staple driver or the staple member to align a second set of staples with the staple driver; and
driving a second set of staples from the staple member towards the anvil,
wherein the first and second sets of staples are arranged symmetrically about the axis.

11. The method of claim 10, wherein the first set of staples includes multiple staples equally spaced from the axis, and the second set of staples includes multiple staples equally spaced from the axis.

12. The method of claim 10, wherein each staple of the first and second sets of staples includes a cross-member, and the cross-members of the first and second sets of staples are aligned in a revolver-type arrangement.

13. The method of claim 10, wherein each staple of the first and second sets of staples includes a cross-member, and the cross-members of the first and second sets of staples are aligned to form a square pattern.

14. The method of claim 10, wherein the stapler includes one or more arm assemblies that couple the staple member and the anvil together, wherein each arm assembly of the one or more arm assemblies includes a proximal section pivotally coupled to the staple member and a distal section pivotally coupled to the anvil, wherein the proximal section and the distal section are pivotally joined together.

15. The method of claim 10, wherein the staple driver is configured to move in a direction parallel to the axis to drive the first and second sets of staples from the staple member.

16. The method of claim 10, wherein driving the first set of staples includes simultaneously driving each staple of the first set of staples, and driving the second set of staples includes simultaneously driving each staple of the second set of staples.

17. A method for stapling tissue, comprising:
inserting a stapler into a body cavity of a patient, wherein the stapler includes an anvil and a staple member spaced from the anvil along an axis, the staple member including a plurality of staples oriented radially with respect to the axis, the plurality of staples including at least a first set of staples and a second set of staples;
driving the first set of staples from the staple member towards the anvil at a first time; and
driving the second set of staples from the staple member towards the anvil at a second time.

18. The method of claim 17, wherein each of the first set of staples and the second set of staples includes two or more staples symmetrically arranged about the axis, and the first set of staples and the second set of staples include an equal number of staples.

19. The method of claim 17, further comprising rotating at least one of a staple driver or the staple member after driving the first set of staples to align the second set of staples with the staple driver.

20. The method of claim 17, further comprising driving a third set of staples of the plurality of staples from the staple member towards the anvil.

* * * * *